US012167979B2

(12) United States Patent
Lum et al.

(10) Patent No.: US 12,167,979 B2
(45) Date of Patent: Dec. 17, 2024

(54) PHACOMACHINE IRRIGATION AND ASPIRATION INTEGRATION FOR CAPSULOTOMY DEVICE

(71) Applicant: Centricity Vision, Inc., Carlsbad, CA (US)

(72) Inventors: Brandon Jay Lum, Fremont, CA (US); Mark Evan Steen, Santa Ana, CA (US); Leonard Richard Borrmann, Capistrano Beach, CA (US); Harold J. Walbrink, Laguna Niguel, CA (US)

(73) Assignee: Centricity Vision, Inc., Carlsbad, CA (US)

( * ) Notice: Subject to any disclaimer, the term of this patent is extended or adjusted under 35 U.S.C. 154(b) by 0 days.

(21) Appl. No.: 17/982,199

(22) Filed: Nov. 7, 2022

(65) Prior Publication Data

US 2023/0140857 A1 May 11, 2023

Related U.S. Application Data

(60) Provisional application No. 63/277,293, filed on Nov. 9, 2021.

(51) Int. Cl.
*A61B 18/08* (2006.01)
*A61F 9/007* (2006.01)
(Continued)

(52) U.S. Cl.
CPC ...... *A61F 9/00754* (2013.01); *A61B 2017/00199* (2013.01); *A61B 2017/00544* (2013.01); (Continued)

(58) Field of Classification Search
CPC ....... A61F 9/00754; A61F 2009/00889; A61B 18/1402; A61B 2018/142;
(Continued)

(56) References Cited

U.S. PATENT DOCUMENTS 5,697,898 A 12/1997 Devine
5,921,999 A 7/1999 Dileo
(Continued)

FOREIGN PATENT DOCUMENTS

WO WO 2016/030023 A1 3/2016

OTHER PUBLICATIONS

PCT International Search Report and Written Opinion, PCT Application No. PCT/US2022/49227, Mar. 27, 2023, 10 pages.
(Continued)

*Primary Examiner* — Jaymi E Della
(74) *Attorney, Agent, or Firm* — Fenwick & West LLP

(57) ABSTRACT

A surgical system for performing a capsulotomy of a lens capsule of an eye includes an elastic ring, a suction cup, an interface, a converter, and a control console. The elastic ring includes a conductive surface. The interface may be coupled to an air port and/or a fluid line of a phacomachine. The converter detects a pulse of air from the phacomachine via the interface, and produce an electrical signal in response. Fluid received from the phacomachine is delivered into the suction cup. The system is configured to remove the fluid from the suction cup and between the suction cup and a surface of the eye to form a suction seal. The control console is configured to, in response to receiving the electrical signal, drive a series of electrical pulses through the conductive surface of the elastic ring, causing the elastic ring to perform a tissue cutting operation.

8 Claims, 17 Drawing Sheets

(51) Int. Cl.
  *A61B 17/00* (2006.01)
  *A61B 17/30* (2006.01)
  *A61B 18/00* (2006.01)
  *A61B 18/14* (2006.01)
  *A61B 90/00* (2016.01)
  *A61F 9/008* (2006.01)

(52) U.S. Cl.
  CPC ............ *A61B 2017/00862* (2013.01); *A61B 2017/00973* (2013.01); *A61B 2017/308* (2013.01); *A61B 2018/00601* (2013.01); *A61B 18/1402* (2013.01); *A61B 2018/142* (2013.01); *A61B 2018/1465* (2013.01); *A61B 2090/064* (2016.02); *A61B 2217/005* (2013.01); *A61B 2217/007* (2013.01); *A61B 2218/002* (2013.01); *A61B 2218/007* (2013.01); *A61F 2009/00889* (2013.01)

(58) Field of Classification Search
  CPC ...... A61B 2018/1465; A61B 2218/002; A61B 2218/007
  See application file for complete search history.

(56) References Cited

U.S. PATENT DOCUMENTS

| | | | |
|---|---|---|---|
| 6,394,974 | B1 | 5/2002 | Kadziauskas et al. |
| 10,363,167 | B2 | 7/2019 | Keller |
| 2009/0216225 | A1 | 8/2009 | Ben-Nun |
| 2010/0280435 | A1 | 11/2010 | Raney et al. |
| 2010/0312252 | A1* | 12/2010 | Jia ................. A61F 9/00754 606/29 |
| 2011/0071524 | A1* | 3/2011 | Keller .............. A61B 18/082 606/107 |
| 2011/0118734 | A1 | 5/2011 | Auld et al. |
| 2013/0197548 | A1* | 8/2013 | Keller .............. A61F 9/00754 606/166 |
| 2014/0128821 | A1 | 5/2014 | Gooding et al. |
| 2014/0207137 | A1 | 7/2014 | Keller |
| 2014/0316389 | A1* | 10/2014 | Schuele ........... A61F 9/00836 606/5 |
| 2015/0190278 | A1 | 7/2015 | Gooding et al. |
| 2016/0106582 | A1 | 4/2016 | Campos et al. |
| 2016/0128758 | A1 | 5/2016 | Keller |
| 2016/0175146 | A1 | 6/2016 | Gooding et al. |
| 2016/0346121 | A1* | 12/2016 | Ianchulev ......... A61F 9/00763 |
| 2018/0064578 | A1* | 3/2018 | Clauson ......... A61B 17/320016 |
| 2018/0228962 | A1 | 8/2018 | Lin |
| 2020/0085619 | A1* | 3/2020 | Schaller .......... A61F 9/00754 |
| 2021/0000497 | A1 | 1/2021 | Keller et al. |
| 2021/0259881 | A1 | 8/2021 | Gray et al. |

OTHER PUBLICATIONS

PCT Invitation to Pay Additional Fees, PCT Application No. PCT/US2022/49227, Jan. 27, 2023, 2 pages.

European Patent Office, Extended European Search Report and Written Opinion, European Patent Application No. 22893513.6, Feb. 27, 2024, 7 pages.

* cited by examiner

PHACOMACHINE IRRIGATION AND ASPIRATION INTEGRATION FOR CAPSULOTOMY DEVICE

CROSS-REFERENCE TO RELATED APPLICATIONS

This application claims the benefit of U.S. Provisional Application No. 63/277,293, filed Nov. 9, 2021, which is incorporated by reference in its entirety.

BACKGROUND

This description generally relates to medical devices and specifically to microsurgical instruments for lens capsulotomies during cataract surgery.

A conventional stand-alone capsulotomy device requires several components to provide its own power, suction, and control capabilities. The stand-alone device may include a control system that includes, for example, a touch screen display, a wireless foot pedal, and/or a wireless remote to control the device. The suction capability may be implemented by a suction module that controls a pump to create suction power for a capsulotomy procedure. Additionally, the stand-alone device may include separate suction, irrigation and/or aspiration tubes. All these components increase the space required in the operating rooms, whereas floor space is at a premium in most operating rooms. Further, the separate control system may complicate the operator's control procedures. For example, an operator may need to switch from a foot pedal that controls a phacomachine to the foot pedal that controls a stand-alone capsulotomy device, which may lower operation efficiency.

Therefore, a capsulotomy system that can be incorporated with a phacomachine may improve efficiency in the operating room and ease of operation to enhance clinical outcome and patient safety.

SUMMARY

Embodiments relate to a microsurgical system for tissue cutting that produces consistent capsulotomies and improves upon current tissue cutting devices. The microsurgical system can be used for smoothly and easily accessing tissue to perform a microsurgery. The system is configured to operate in conjunction with a phacoemulsification machine (phacomachine) for cutting tissue, for example, creating excisions in the eye's anterior lens capsule membrane during an eye cataract surgery. The system offers benefits in terms of ergonomic efficiency in the operating room and ease of operation to enhance clinical outcome and patient safety.

A capsulotomy system can include a capsulotomy handpiece, a converter, a control console, and an interface. The functional end of a capsulotomy handpiece may contain an elastic ring for performing capsulotomies. The elastic ring is configured for cutting tissue and includes a conductive surface on a bottom of the elastic ring. The interface may include one or more connectors configured to couple to a vitrector air port of a phacomachine. The vitrector air port on the phacomachine is connected to a converter that detects a pulse of air from the phacomachine's vitrector port. Air pulse detection produces an electrical signal that is sent to the control console. The control console is configured to, in response to receiving the electrical signal, drive a series of electrical pulses through the conductive surface of the elastic ring, causing the elastic ring to perform a tissue cutting operation.

A method for performing a microsurgery using the capsulotomy system includes detecting a pulse of air from a phacomachine using a converter of the capsulotomy system. The capsulotomy system includes an interface configured to couple to an air port, for example the vitrector port of the phacomachine to receive the pulse of air. The method further includes producing, by the converter, an electrical signal in response to detecting the pulse of air; and driving, by a control console of the capsulotomy system, a series of electrical pulses to an elastic ring of the capsulotomy system to perform a tissue cutting operation. The control console may drive the electrical pulses based on the produced electrical signal from the converter.

In some embodiments, the method for performing a microsurgery using the capsulotomy system includes using the phacomachine's foot pedal to control the initiation of an air pulse delivered through its vitrector port. This air pulse can then be detected using the capsulotomy's converter and used to generate a series of electrical pulses to an elastic ring of the capsulotomy system to perform a tissue cutting operation.

In one aspect, this disclosure presents a capsulotomy system that includes an elastic ring, a suction cup, an interface, and a control console. The elastic ring is coupled to a stem and includes a conductive surface for cutting tissue. The suction cup is coupled to the elastic ring. The interface is coupled to a fluid line of a phacomachine and configured to receive fluid from the suction cup. The control console is configured to deliver the received fluid to a space between the suction cup and a surface of an eye.

In another aspect, the interface is coupled to a fluid aspiration or suction line of a phacomachine and configured to remove at least a portion of fluid from the suction cup. The control console through its use of the aspiration functions of the phacomachine, is configured to remove the fluid from the space between the suction cup and the surface of the eye to form a suction seal between the suction cup and the surface of the eye; and after the suction seal is formed, the capsulotomy system drives a series of electrical pulses through the conductive surface of the elastic ring to perform the capsulotomy. In some embodiments, the aspiration functions of the phacomachine can be controlled by the use of a foot pedal. In this manner, the foot pedal can be used to control the aspiration required for the creation of the appropriate seal between the suction cup with the elastic ring and the capsule surface for the operation of a capsulotomy.

A method for performing a microsurgery using the capsulotomy system includes receiving fluid from a fluid line (e.g., irrigation line) of a phacomachine. The irrigation fluid from the phacomachine is delivered to the capsulotomy system. The method further includes delivering the received fluid into a space between a suction cup of the capsulotomy system and a surface of an eye. The delivery of this irrigating fluid can also be controlled by a foot pedal of the phacomachine. Fluid delivered in this manner to the capsulotomy system may serve a multitude of purposes including but not limited to repositioning the suction cup onto a different location on a surface of the eye, removing viscous material such as ophthalmic surgical device from under the suction cup, maintaining the pressure inside the eye during surgery, and reversing the suction created by the aspiration of fluid.

Figure 1A:
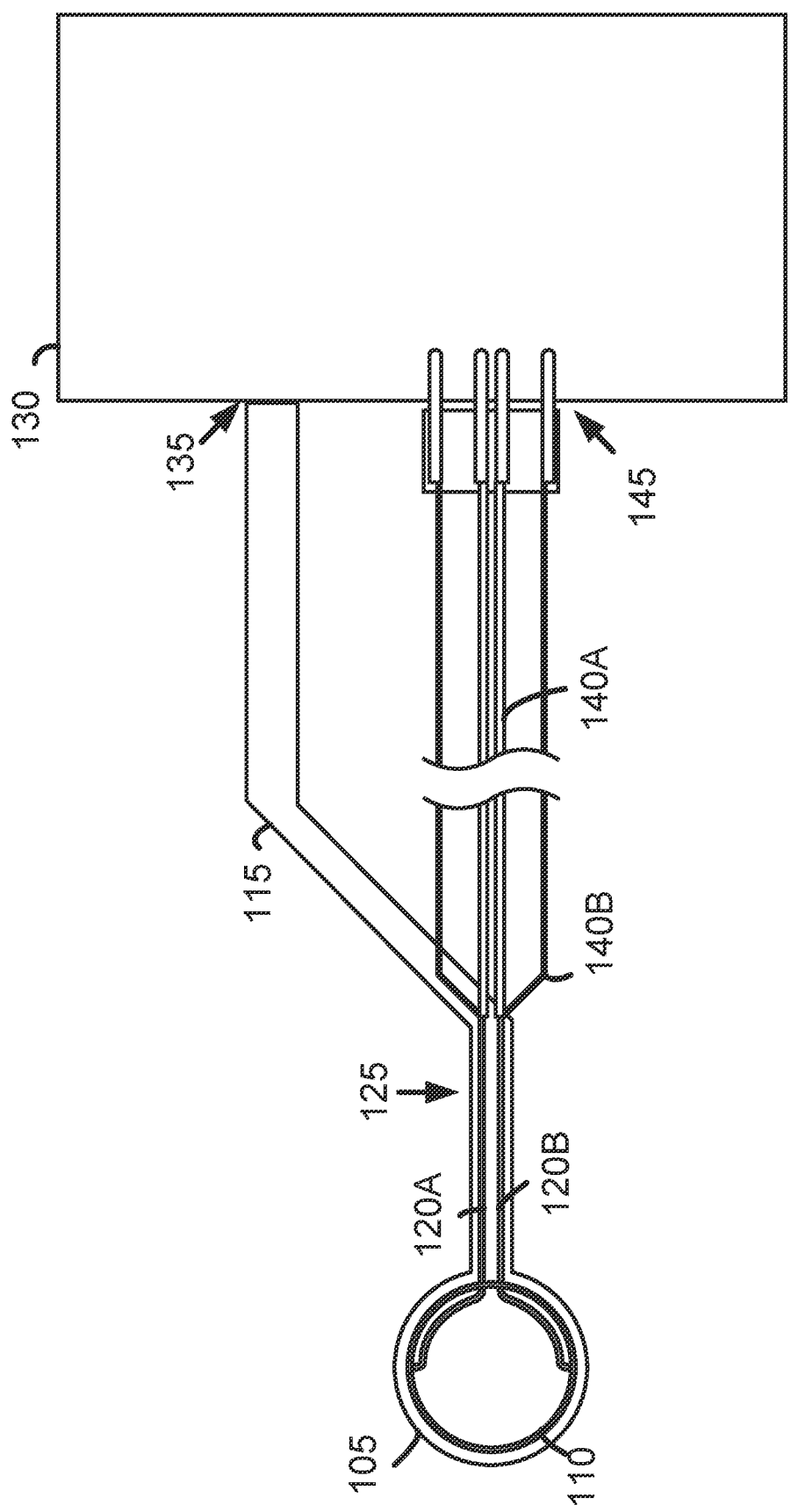
FIG. 1A illustrates a microsurgical device connected to its control console, according to one embodiment.

The figures depict various example embodiments of the present technology for purposes of illustration only. One skilled in the art will readily recognize from the following description that other alternative embodiments of the structures and methods illustrated herein may be employed without departing from the principles of the technology described herein.

DETAILED DESCRIPTION

Embodiments described herein relate to a microsurgical system for cutting tissue that that performs a capsulotomy. In some embodiments, the microsurgical system may be incorporated with a phacomachine in which an air pulse delivered from a vitrector port of the phacomachine can be sensed by a converter of the microsurgical system. The detected signal triggers the capsulotomy function in the microsurgical system and delivers a series of electrical pulses to perform the capsulotomy. In one example, the phacomachine includes a foot pedal that controls the generation of air pulses from the phacomachine. In this way, full control of all aspects of the capsulotomy procedure are completely within the control of an operator using the phacomachine foot pedal.

In addition to control of suction and energy delivery, the microsurgical system and the phacomachine can be programmed at the operator's discretion to automate certain aspects of the capsulotomy procedure, e.g., push rod retraction, identification of full suction, automatic energy delivery on maximum suction, verbal confirmation of achievement of key procedural steps, etc. The procedure can be automated depending on operator preference by the operator's phacomachine's foot pedal, which reduces the operator's learning curve as the operator is using the phacomachine foot pedal they are accustomed to using.

Further, the ability to add the microsurgical system largely within the footprint of the existing a phacomachine saves space and provides the circulator and scrub technician easy access for a surgery. The integration of the microsurgical system and a phacomachine provides the opportunity to use less tubing and still be able to manage any operating room requirements. The integration also simplifies the consumables and eliminates the need for a syringe, a roller pump, and a fluid isolator necessary to manually release suction and protect the microsurgical device from fluid ingress, thus improving ergonomic efficiency in the operating room.

In some embodiments, the microsurgical system may include irrigation and/or aspiration tubes that can be integrated with fluid lines of a phacomachine. The irrigation tube may receive fluid from the fluid line and inject the fluid into an anterior chamber of the eye, for example to maintain the pressure within the anterior chamber, amongst other uses.

Further, the irrigation and/or aspiration functions can assist in removing or diluting the viscous Ophthalmic Surgical Device (OVD) present under the suction cup. OVD is a viscous gel-like material used in surgery to protect endothelial cells. Removing high viscosity OVD from under the suction cup will help the suction cup to attach to the capsule surface once suction is activated by the operator. The irrigation and/or aspiration functions may also assist the reversal of suction to lift the suction cup off the capsule after capsulotomy, or if an operator desires to re-position the capsulotomy in a different location on the capsule. Collection of trapped air bubbles in the microsurgical system and in the anterior chamber hinder operator visualization of the surgical field. The ability to irrigate helps to remove the air bubbles in the microsurgical system, the anterior chamber, as well as the presurgical setup.

Figure 1B:
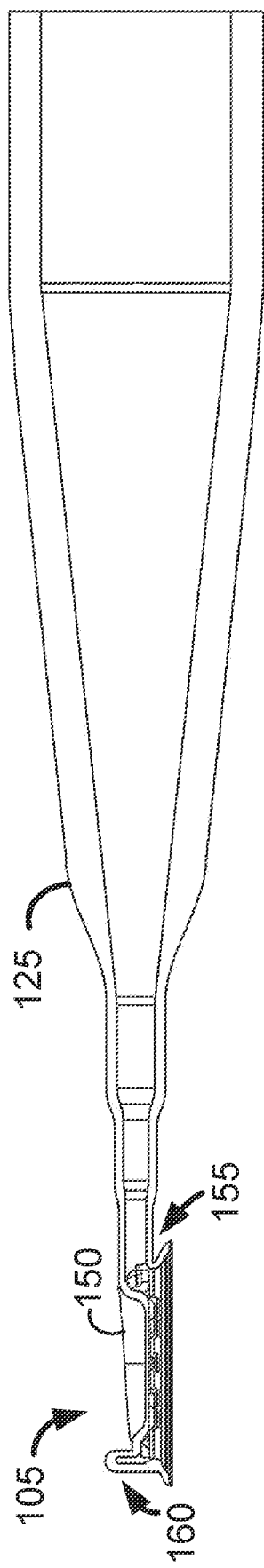
FIGS. 1B-1C illustrate cross-sectional views of the microsurgical device shown in FIG. 1A, according to one embodiment.
Figure 1C:
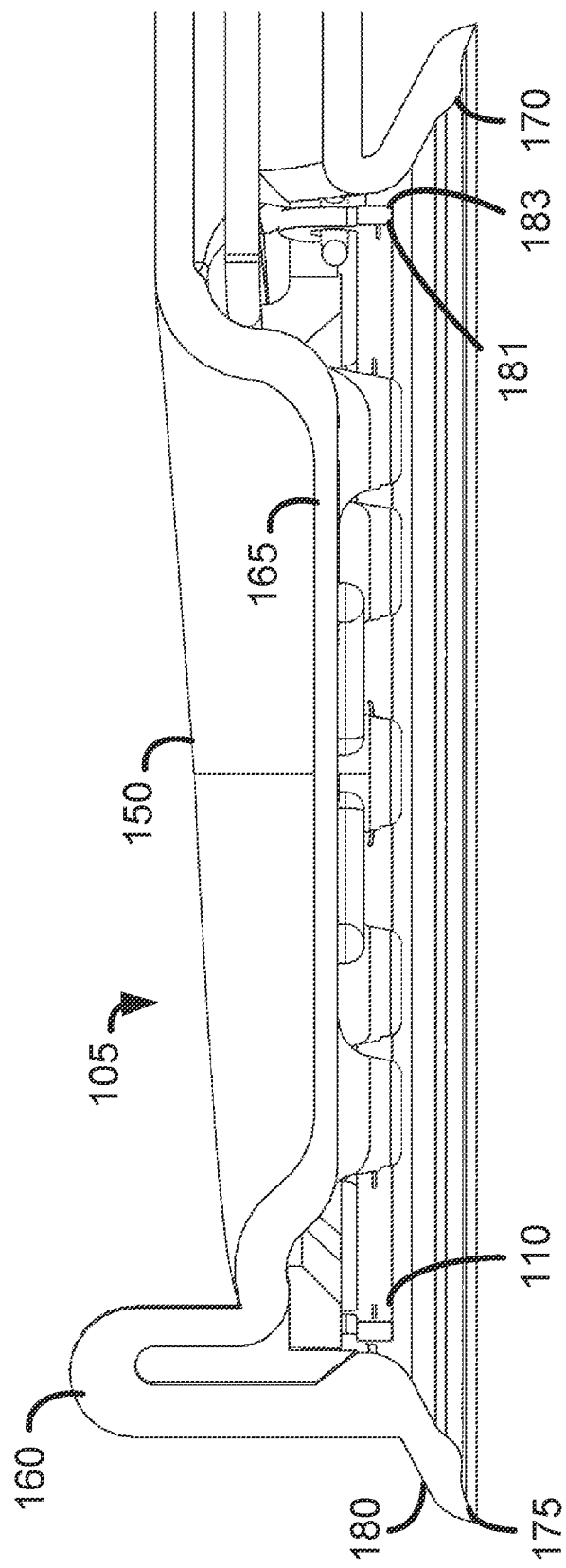
Figure 1D:
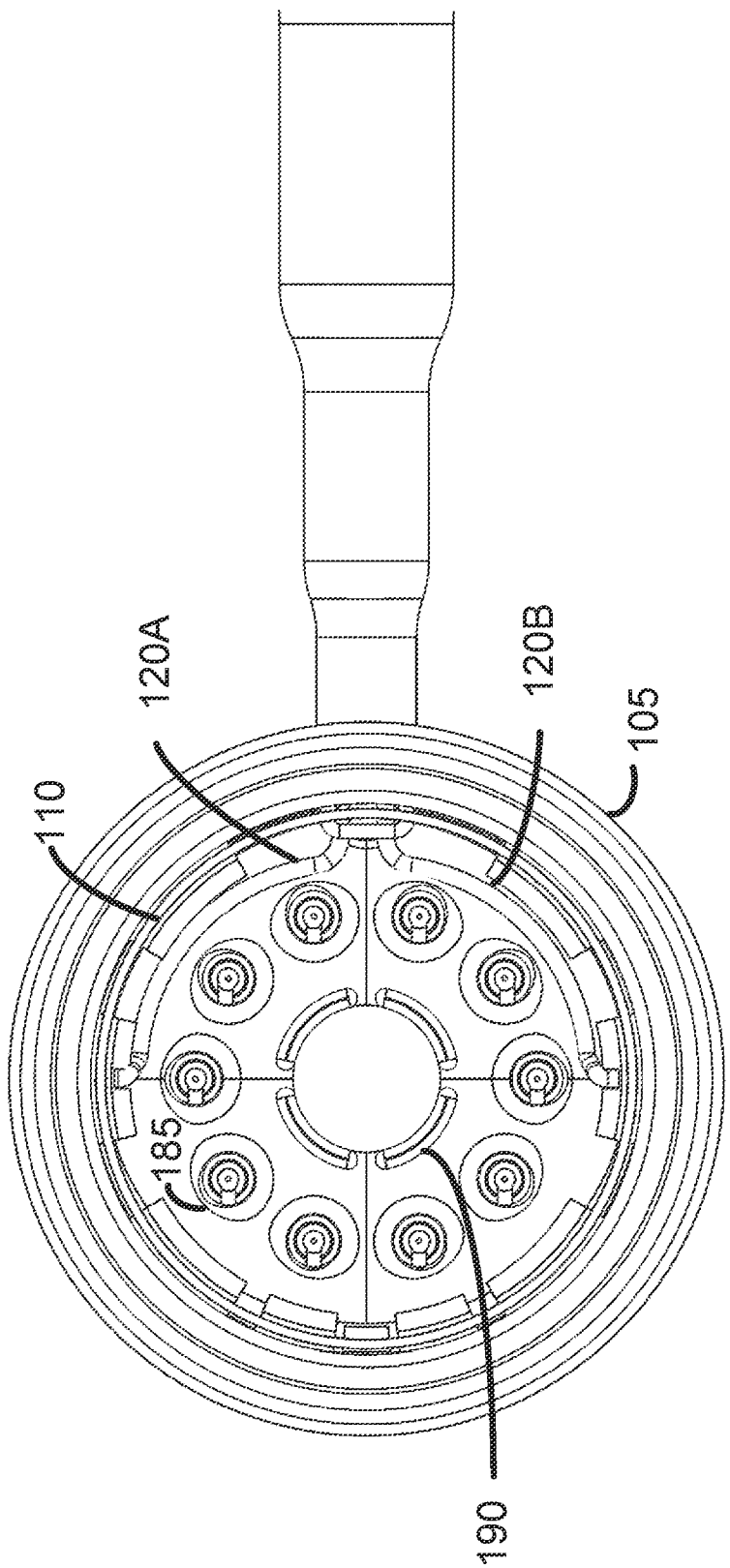
FIG. 1D illustrates a bottom view of the microsurgical device shown in FIG. 1A, according to one embodiment.
Figure 1E:
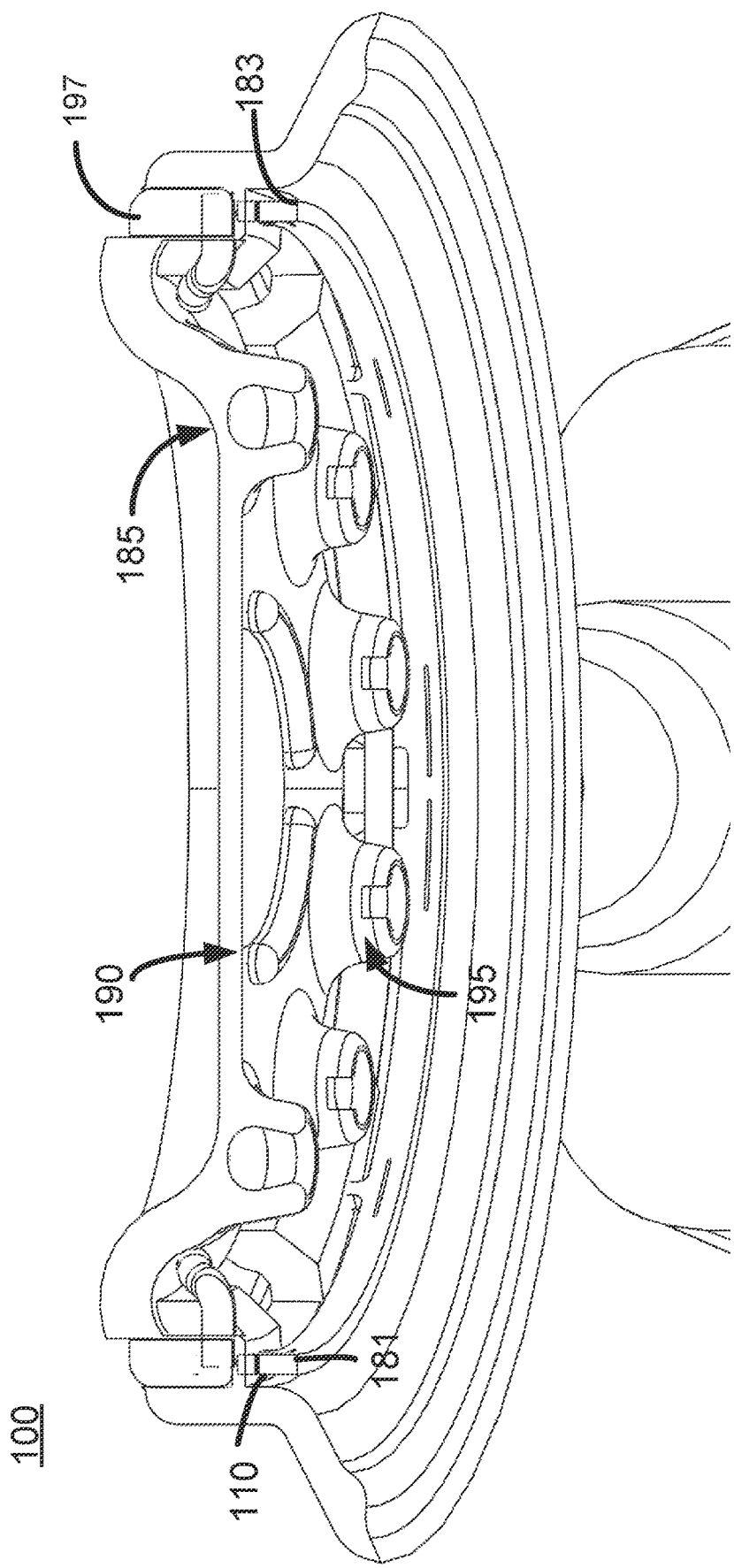
FIG. 1E illustrates a bottom perspective view of the microsurgical device shown in FIG. 1A, according to one embodiment.
Figure 1F:
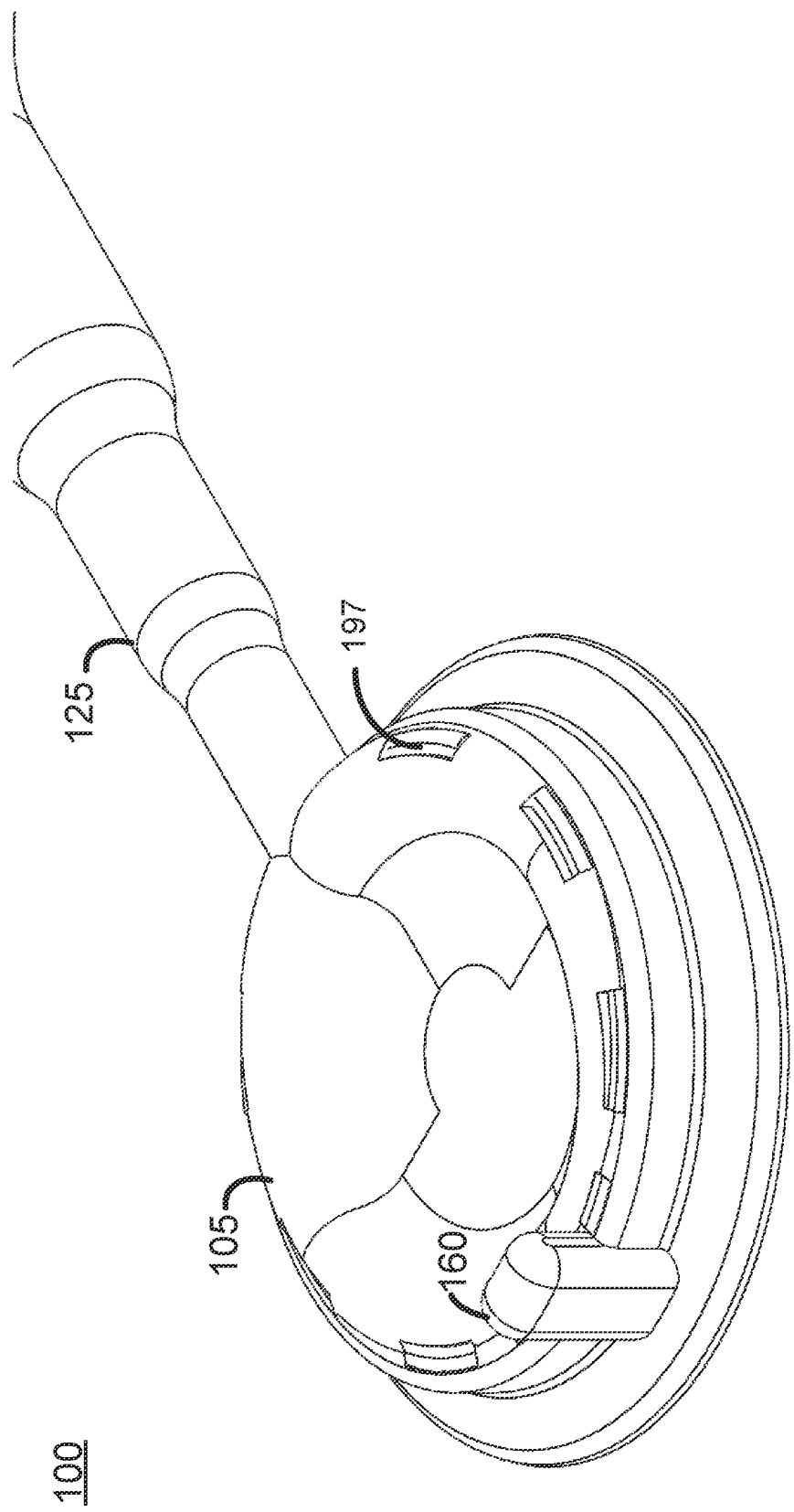
FIG. 1F illustrates a top perspective view of the microsurgical device shown in FIG. 1A, according to one embodiment.

Figures (FIGS. 1A-1F illustrate various views of a microsurgical device 100 for tissue cutting. FIG. 1A illustrates an embodiment of a microsurgical device 100. FIGS. 1B-1C illustrate cross-sectional views of the microsurgical device 100. FIG. 1D illustrates a bottom view of the microsurgical device 100. FIG. 1E illustrates a bottom perspective view of the microsurgical device 100. FIG. 1F illustrates a top perspective view of the microsurgical device 100.

The device 100 shown in FIG. 1A includes a suction cup 105, a cutting element 110 (also referred to as "cutting ring" herein), one or more suction tubes 115, electrical leads 120A, 120B, and a stem 125. The suction cup 105 and cutting element 110 are located at a distal end of the stem 125, which houses the one or more suction tubes 115 and the electrical leads 120A, 120B. The device 100 further includes a control console 130 (also referred to as "controller" herein) that is configured to provide suction to the suction cup 105 and electrical energy to the cutting element 110. The suction cup 105 is connected to the control console 130 via the one or more suction tubes 115 and a suction connector 135. The cutting element 110 is connected to the control console 130 via the electrical leads 120A, 120B, one or more sets of electrical conductors, such as electrical conductors 140A, 140B, and an electrical connector 145.

The suction cup 105 is a foldable structure that can provide a water-tight seal between the edges of the suction cup 105 and the tissue being excised (e.g., lens capsule, corneal tissue, connective tissue, and the like). Because of the fluidic seal between the suction cup 105 and the tissue, vacuum or fluidic pressure can be applied to the suction cup 105 and the tissue so that the resulting pressure presses the cutting element 110 against the tissue. Pressing the cutting element 110 against the tissue facilitates a more precise, smoother cut. The foldable structure of the suction cup 105 is reversibly collapsible such that a cross-section of the suction cup 105 can decrease for insertion of the device 100 through an incision. As such, the suction cup 105 may include a compliant material, such as silicone, polyurethane, and the like. In one embodiment, the material of the suction cup 105 is a medical grade silicone having a Shore A durometer of 60 (e.g., Nusil MED-4960). Further, the silicone may be clear, which may assist in the placement of the suction cup 105.

The cutting element 110 is an element designed to cut tissue through application of pressure and/or electrical current via one or more electrical leads 120A, 120B coupled to the cutting element 110. The cutting element 110 can be made from various materials. In some embodiments, the metallic components of the cutting element 110 may be made by electroforming suitable materials such as nickel, nickel-titanium alloys, gold, steel, copper, platinum, iridium, molybdenum, tantalum, and the like. When the cutting element 110 is configured to electrically excise tissue, the material for the cutting element 110 is electrically conductive. In addition, the cutting element 110 is reversibly collapsible such that a cross-section of the cutting element 110 can decrease for insertion of the device 100 through an incision. Therefore, the material of the cutting element 110 is generally elastic so that it can return to its original shape after insertion of the device 100 through the incision. A typical construction example is a superelastic nitinol ring having a wall thickness of 0.075 mm, height of 0.140 mm, and tabs. Another strategy is to add to this superelastic body a thin film (e.g., 0.0001 to 0.002 mm) of a more conductive material that does not have to be superelastic because it is very thin. Examples of materials include, but are not limited to, spring steel, stainless steel, titanium nickel alloy, graphite, nitinol, nickel, nickel-chrome alloy, tungsten, molybdenum, tantalum, gold, silver, or any other material that will allow the cutting element 110 to return to its prior shape.

The device 100 is capable of delivering a wide range of energies (e.g., from 0 to 3 joules, or more) via the cutting element 110. The energy dissipated by the cutting element 110 during use in surgery may be determined empirically through use on a specific tissue of interest. For example, in a capsulotomy of the anterior lens capsule of an adult human, it was found that about 1.2 joules produced a satisfactory result. Some specific example of applications to lens capsulotomies include pediatric as well as adult humans and other animals such as dogs, listed in order of increasing energy need. To accommodate the varying energy needs, the amount of energy dissipated by the cutting element 110 may be controlled by controlling parameters such as the number of pulses, duration of each pulse, time between pulses, and/or energy of each pulse applied to the tissue via the cutting element 110. These parameters may be determined empirically for each tissue application and/or via computational modeling. In addition, temperature gradients in the cutting element 110 may be designed and/or modified for different tissues.

The one or more suction tubes 115 are located within the stem 125 of the device 100. The one or more suction tubes 115 are configured to provide suction to the suction cup 105. The one or more suction tubes 115 provide suction to the suction cup 105 to cause the suction cup 105 to be collapsed and create a suction seal. The one or more suction tubes 115 may also be configured to reverse the suction and/or fluid flow being applied to the suction cup 105 to disengage the suction cup 105 and cutting element 110 from the excised tissue. In some embodiments, the material of the suction tubes 115 is a medical grade silicone having a Shore A durometer of 60 (e.g., Nusil MED-4960). In some embodiments, the electrical leads 120A, 120B, an anchor thread, and/or a rigid extender run through the one or more suction tubes 115 to the suction cup 105.

The one or more suction tubes 115 may be further configured to act as fluid paths. For example, the one or more suction tubes 115 may be primed before use with a solution, such as a balanced salt solution. Priming the fluid paths of the one or more suction tubes 115 may help ensure that there is little to no compressible air in the device 100. In addition, after excision of the tissue is complete, a hydraulic release of the one or more suction tubes 115 may be performed to release the suction cup 105 from the tissue. In some embodiments, the hydraulic release consists of forcing 0.05 ml to 0.2 ml of a balanced salt solution from the suction tubes 115 back into the suction cup 105.

In some embodiments, the device 100 may further include one or more fluid tubes configured to receive fluid. The fluid tubes and the suction tubes 115 may connect to the stem 125 at a same connection point. The fluid tubes and the suction tubes 115 may be switched to connect to the stem 125. Inside the stem 125, the fluid tubes and the suction tubes 115 may share the same channel that is coupled to the suction cup 105. Alternatively, the fluid tubes and the suction tubes 115 may connect to the stem 125 at different connection points, for example, at the opposite ends of the stem 125. In another example, the fluid tubes include an inlet coupled to the suction cup 105 and the suction tubes 115 include an outlet coupled to the suction cup 105. The inlet of the fluid tubes is different from the outlet of the suction tubes 115 so that the fluid tubes and the suction tubes 115 can be operated at the same time.

The configuration of the one or more suction tubes 115 along the inner surface of the suction cup 105 may vary. For example, when there are two or more suction tubes 115, the suction tubes 115 may be located at antipodal points of the suction cup 105. This configuration may ensure equal distribution of suction throughout the suction channels of the suction cup 105. In other embodiments, the suction tubes 115 may be adjacent, located within a threshold number of degrees of each other, located within a threshold distance of each other, and the like. Further, the suction tubes 115 may be located along an outer surface of the suction cup 105, along a bottom surface of the suction cup 105, along a top surface of the suction cup 105, and the like. In embodiments where the device 100 includes a single suction tube 115, the suction tube may be located at any point along the inner surface of the suction cup 105. For example, an orifice of the suction tube 115 may be located in a roof of the suction cup 105, at a proximal end of the suction cup 105, at a distal end of the suction cup 105, and the like.

The electrical leads 120A, 120B are configured to provide electrical energy to the cutting element 110. The electrical leads 120A, 120B are located within the stem 125 of the device 100 and coupled to a surface of the cutting element 110. In some embodiments, the electrical leads 120A, 120B are silver wires. In other embodiments, the electrical leads 120A, 120B are made of copper, aluminum, gold, or the like. In addition, the electrical leads 120A, 120B may insulated.

The control console 130 is configured to provide suction to the suction cup 105 and electrical energy to the cutting element 110. In addition, an operator of the device 100 may control the depth of cut via the control console 130 by modifying the suction and/or electrical parameters of the device 100.

Suction is provided to the suction cup 105 via one or more suction tubes 115 connected to the control console 130 and a suction connector 135. Using the control console 130, an operator of the device 100 may provide suction to the suction cup 105, reverse suction during disengagement of the device 100, and/or flush the fluid paths of the one or more suction tubes 115 with a solution. In addition, an operator of the device 100 may modify the amount of suction applied to the suction cup 105 based on the operation being performed. In some embodiments, an operator of the device 100 may manually modify the amount of suction applied to the suction cup 105, for example using a vacuum valve and/or a vacuum gauge of the control console 130. Alternatively, or additionally, the control console 130 may include predetermined suction parameters determined via experimentation, modeling, and/or a combination thereof that are each associated with a procedure. In addition, using the control console 130, different amounts of suction may be provided to different suction tubes. By way of example, suction pressure of 19+/−1 inch of Hg vacuum has been used successfully. That is gauge pressure, not absolute pressure, so the same pressure differential is established by the control console 130 across the suction cup wall regardless of altitude at which it is used. Further, as described below, the pressure applied may be fluidic pressure.

The control console 130 delivers electrical energy to the cutting element 110 via the electrical leads 120A, 120B, one or more sets of electrical conductors 140A, 140B, and an electrical connector 145. A first set of electrical conductors 140A may be configured to provide power to the cutting element 110. A second set of electrical conductors 140B may be for resistance measurement and may be connected to a measurement device, such as a Kelvin probe (also known as the 4-wire resistance measurement method). In some embodiments, the first set of electrical conductors 140A and/or the second set of electrical conductors 140B are copper wires, such as (respectively) 24 ga copper wires, 30 ga copper wires, and the like. In other embodiments, the first set of electrical conductors 140A and/or the second set of electrical conductors 140B are composed of aluminum, gold, silver, or the like. Electrical energy may be provided to the cutting element 110 as one or more electrical waveforms. The one or more electrical waveforms are discharged through the cutting element 110 to cause the cutting element 110 to heat up for a short time, such as 0.0001 seconds to 0.05 seconds, depending on the applied voltage and current.

Using the control console 130, the depth of cut may be controlled by controlling the amount of electrical discharge applied to the cutting element 110. For example, the depth of cut may be controlled by modifying one or more of: the energy of each pulse, the number of pulses in the pulse train, the inter-pulse intervals, and the like. As with the suction, these parameters may be manually modified by an operator of the device 100 using control elements of the control console 130. Alternatively, or additionally, the control console 130 may include predetermined sets of parameters that are each associated with different depths of cut, different patient types, and the like. These sets of parameters may be determined through experimentation, modeling, and/or a combination thereof. The control console 130 may be a controller, microprocessor, a programmable hardware logic, etc.

In some embodiments, the control console 130 may change the operating parameters of the device 100 automatically. For example, the control console 130 may change the operating parameters according to a predetermined set of operating steps associated with a procedure. Alternatively, or additionally, the control console 130 may change the operating parameters of the device 100 based on feedback from the device 100 itself. For example, the control console 130 may change the operating parameters of the device 100 in response to a detection of a device resistance, a pressure, a pressure change, a temperature, a temperature change, a determined depth of cut, or the like, during use.

In some embodiments, the device 100 may further include a converter. The converter is coupled to an interface which further couples to a phacomachine. The converter detects a pulse of air from the phacomachine through the interface and covert the pulse of air to an electrical signal. The control console 130 which couples to the converter receives the electrical signal and delivers electrical pulses to the cutting element 110.

FIG. 1B illustrates a cross-sectional view of the device 100. In the embodiment shown, a height of the proximal end of the suction cup 105 is greater than a height of a distal end of the suction cup 105, forming a tapered circumferential suction chamber 150 in the suction cup 105. The tapered circumferential suction chamber 150 helps ensure even suction is applied, in part, because the height of the chamber decreases as the volume to be evacuated reduces.

In some embodiments, a first height of the tapered circumferential suction chamber 150 may have a first height at an orifice of the suction cup 105 and a second height at an antipodal point of the suction cup. In these embodiments, the first height may be larger than the second height. For example, the height of the suction cup 105 may be greatest at the proximal end and shortest at the distal end. In some embodiments, the relative heights of the proximal end of the suction cup 105 and the distal end of the suction cup 105 may be based on a number of factors, including, but not limited to: the amount of total volume to be evacuated, the amount of suction being applied, the type of procedure being performed, the type of tissue being excised, the amount of electrical energy being applied, features included on the underside of the suction cup 105 (e.g., standoffs and/or visual guides), or the like. For example, the tapered circumferential suction chamber 150 may slope at an angle so that the volume to be removed from the suction cup is proportional to the volume of the tapered circumferential suction chamber 150 along a horizontal axis of the suction cup 105. Examples of the slope angle include, but are not limited, 0 degrees, 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, or 15 degrees.

Figure 3A:
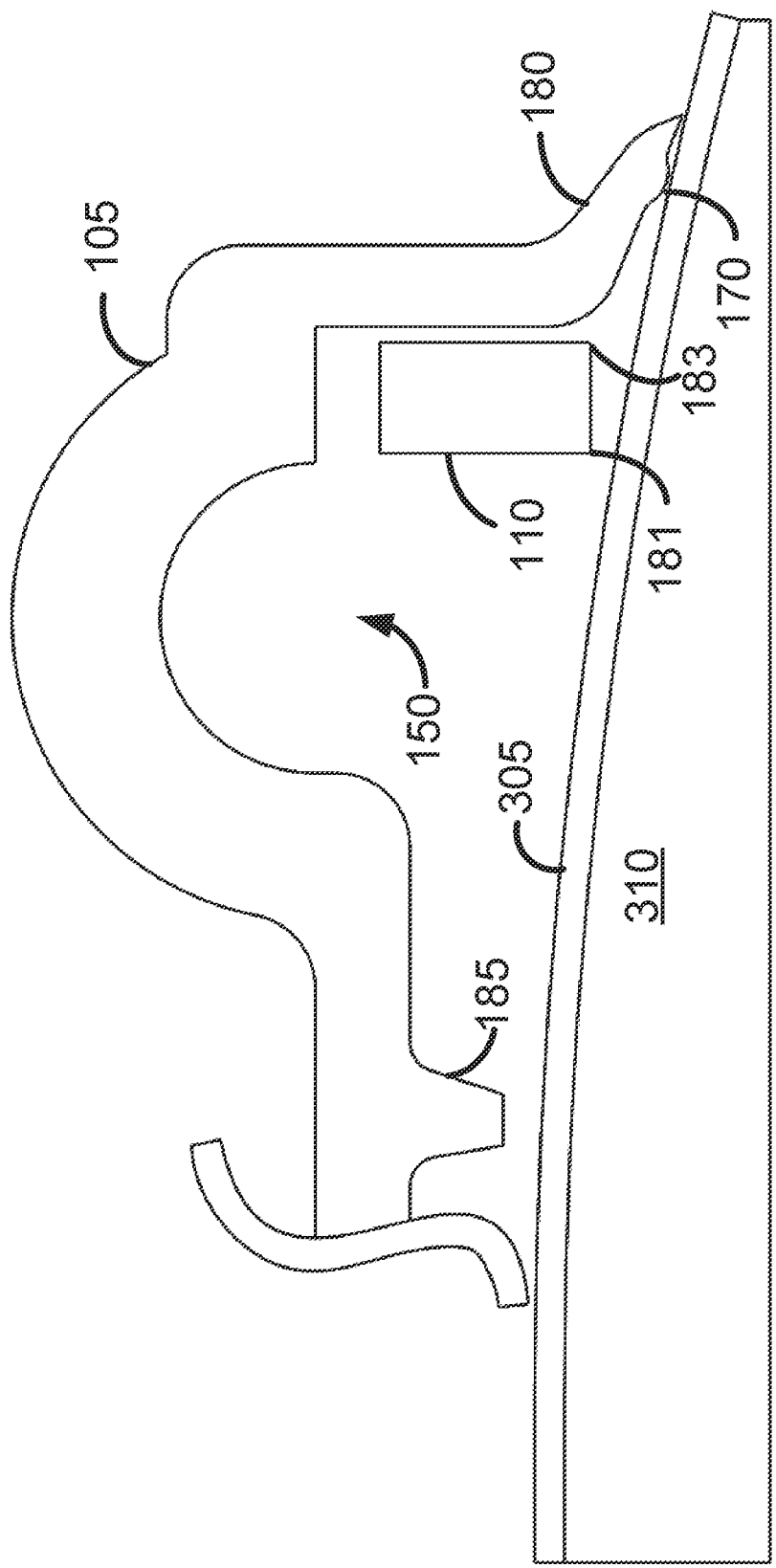
FIG. 3A-3F illustrate the cross-sectional views of one area of the microsurgical device shown in FIG. 1, according to one embodiment.

In addition, the geometry and specifications of the suction cup 105 may be modified to prevent collapse of the suction cup 105 when suction is applied. For example, the top of the tapered circumferential suction chamber 150 may be arched to prevent collapse, as shown in FIG. 3A. The rise and span of the arched portion may vary based on factors including, but not limited to the amount of suction being applied, the type of procedure being performed, or the like.

In addition, the thickness of the suction cup 105 may be modified to prevent collapse when suction is applied. In some embodiments, the thickness of the entire suction cup 105 is a uniform thickness that prevents collapse of the entirety of the suction cup (e.g., 200 microns or more, 175 microns or more, 150 microns or more, 125 microns or more, 100 microns or more, 75 microns or more, 25 microns or more, etc.). In other embodiments, portions of the suction cup may have various thicknesses. For example, portions that should not collapse during use, such as an arched portion of the suction cup 105, may be relatively thicker than other portions of the suction cup 105 that are collapsible during use. In these embodiments, the portions that have an increased thickness may have a thickness around 200 microns or more. Other portions of the suction cup may have thicknesses around 200 microns or less, such as 175 microns or less, 150 microns or less, 125 microns or less, 100 microns or less, as 75 microns or less, 50 microns or less, 25 microns or less, or the like. By limiting the portions of the suction cup 105 that have increased thicknesses, the total amount of silicon required to manufacture the suction cup 105 is reduced and collapse of the suction cup 105 is prevented. Further, by reducing the amount of silicon, the force needed to insert the suction cup 105 through an incision is reduced.

The stem 125 is coupled to the proximal end of the suction cup 105 via an opening within a tapered side of the suction cup 105. A neck 155 of the stem 125 enables the flow of fluid to and from the stem 125 into the suction cup 105 in a direction substantially perpendicular to the direction of the suction force being applied against the tissue. For example, the angle between the flow of fluid to and from the stem 125 and the direction of the suction force being applied against the tissue may be between 85 degrees and 95 degrees, between 80 degrees and 100 degrees, and the like. The substantially perpendicular flow helps ensure uniform distribution of suction. In alternative embodiments, the neck 155 of the stem 125 may be configured to provide substantially vertical flow. In these embodiments, an additional mechanism may be coupled to the neck 155 of the stem 125 to facilitate horizontal flow of suction and/or fluid to the suction cup 105 from the stem 125.

As previously discussed, the device 100 may include a rigid extender (not shown) that is used to extend the cutting element 110 for insertion of the device 100 through an incision, such as a corneal incision. The end of the rigid extender may include one or more prongs to which the cutting element 110 is coupled. The one or more prongs may prevent substantial decoupling of the rigid extender and cutting element 110 during transport. However, the length of the one or more prongs may necessitate a containment pocket 160 that prevents the one or more prongs from puncturing the suction cup 105.

A basic principle of injection molding in device manufacturing is that the intended molded part must not have features that create significant undercuts and prevent the separation of the two mold halves and retrieval of the molded part. In certain cases, the use of side pins may create the desired molded features but involve greater cost and may impart less precision. A horizontal containment pocket may represent a significant undercut and may not be able to be manufactured using standard molding techniques with two mold halves that separate in a vertical direction.

To remove the presence of an undercut created by a horizontal containment pocket, the containment pocket 160 may be collapsible between a vertical position and a horizontal position. In some embodiments, the containment pocket 160 may be collapsible between horizontal and vertical positions because of the flexibility of the material of the containment pocket 160. In alternative embodiments, the containment pocket 160 may be collapsible because of one or more joints, or any other suitable collapsing mechanism. For ease of manufacturing, the containment pocket 160 may be molded in the vertical position. The vertical position of the containment pocket 160 helps ensure the containment pocket is easily released as the two mold halves are pulled in a vertical direction to separate. When the containment pocket 160 is collapsed into the horizontal position, it can accept the end of the rigid extender. In some embodiments, the containment pocket 160 is constrained to lie horizontally during transport. It may remain horizontal as the suction cup 105 and cutting element 110 are elongated via a rigid extender. As the rigid extender is retracted, the containment pocket 160 returns to its vertical as molded shape due to silicone's elasticity.

FIG. 1C illustrates an additional cross-sectional view of the device 100. As discussed with reference to FIG. 1B, the suction cup 105 may form a tapered circumferential suction chamber 150 that slopes downward in a direction from the proximal end to the distal end of the suction cup 105. In addition, a central portion 165 of the suction cup 105 may have a shorter height than the tapered circumferential suction chamber 150 of the suction cup 105. The shortened height of the central portion 165 may reduce the amount of material needs to be evacuated from within the space enclosed by the suction cup 105, which facilitates a more uniform distribution of suction. In some embodiments, the entirety of the central portion 165 may be of uniform height. In alternative embodiments, the central portion 165 may slope at the same angle as the tapered circumferential suction chamber 150 or at a different angle as the tapered circumferential suction chamber 150. In addition, the height (s) of the central portion 165 may vary based on the amount of total volume to be evacuated, the amount of suction being applied, the type of procedure being performed, the type of tissue being excised, the amount of electrical energy being applied, features included on the underside of the suction cup 105 (e.g., standoffs and/or visual guides), or the like.

As illustrated in FIG. 1C, the suction cup 105 includes a sealing contact 170 and a tapered edge 175 along the skirt 180 of the suction cup 105. The compliant skirt 180 enables the sealing contact 170 to remain on the capsular membrane even if a handpiece of the device 100 is rotated or translated by an operator of the device 100. The tapered edge 175 may facilitate the placement of the compliant skirt 180 under the iris, e.g., for procedures involving small pupils. In some embodiments, the tapered edge 175 is where a mold parting line is located. The distance between the tapered edge 175 and the sealing contact 170 may be such that flash from the molding process is not long enough to reach the sealing contact 170. For example, a flash|up to 0.25 mm long will not get between the seal and the capsule and cause a leak.

As further illustrated in FIG. 1C, the proximity of the cutting element 110 to the suction cup 105 may help ensure that only inner bottom edge 181 of the cutting element 110 is in physical contract with the tissue being excised (e.g., a capsular membrane). For example, the cutting element may be coupled to a surface of the suction cup such only the inner bottom edge 181 of the cutting element is in contact with the tissue being excised. In these embodiments, upon application of suction to the suction cup 105, the outer diameter of the cutting element 110 is not in physical contact with the tissue being excised. In these embodiments, the outer diameter of the cutting element 110 affects tissue excision remotely through conduction. For example, the outer diameter of the cutting element 110 may be located at a sufficient distance from the capsular membrane to remotely affect the capsular membrane by a temperature change. The temperature change may assist in the creation of a consistent rolled edge, discussed below with reference to FIGS. 3A-3F. In other embodiments, the coupling of the cutting element 110 and suction cup 105 may be configured such that the outer bottom edge 183 of the cutting element excises the tissue, both the inner bottom edge 181 and outer bottom edge 183 excise the tissue, or any other suitable portion of the cutting element 110 excises the tissue.

FIGS. 1D-1F illustrate additional views of the device 100. As shown in FIG. 1D, the cutting element 110 and electrical leads 120A, 120B are installed. In some embodiments, the electrical leads are electrically insulated silver wires (e.g., 6-micron thick layer of polyimide). In some embodiments, the electrical leads 120A, 120B are pushed back near the top of the interior flow chamber to be out of the way of the cutting edge (e.g., the inner bottom edge 181) of the cutting element 110.

The suction cup 105 shown includes one or more features. Features shown may include hollow standoffs, such as hollow standoff 185, and aiming guides, such as aiming guide 190. In the embodiment shown, the hollow standoffs are placed on an inner surface of the suction cup 105. The hollow standoffs prevent the central portion 165 of the suction cup 105 from completely sealing against the capsular membrane surface, creating channels for material flow and a uniform distribution of suction. In addition, the hollow standoffs may provide a visual indication of the suction level within the suction cup 105. As suction develops, the trapped air bubble is removed from the inside of the hollow standoff. The escape of the air bubble can be used as a visual signal that adequate suction has been developed. The dimensions of the standoffs and aiming guides be varied to select one that traps air bubbles and allows escape only when the desired level of suction has been applied. In some embodiments, the dimensions of the standoffs may vary such that they provide a visual indication of different levels of suction.

In the embodiment shown, the suction cup 105 includes ten stand-offs. In alternative embodiments, the suction cup 105 may include any suitable number of standoffs, such as one standoff, five standoffs, or the like. In some embodiments, the standoffs have a high aspect ratio air traps (e.g., 0.2 mm diameter and 0.3 mm height). In alternative embodiments, the standoffs have low aspect ratio air traps, intermediate aspect ratio air traps, and the like. Further, the aspect ratio can be modified to ensure that air is always trapped. Because silicone rubber is stretchable, the standoff opening can have a smaller diameter than the trap cavity and still be moldable. Reduced diameter at the opening of the standoff may help ensure that air will be trapped until suction reaches the pressure needed for a successful capsulotomy. However, the diameter of the cavity may include smaller and/or equal dimensions as the standoff opening.

In some embodiments, the standoffs include a slot, e.g., slot 195. The slots face away from the stem 125 and/or suction tubes 115. In alternative embodiments, the slots may face the stem and/or suction tubes 115, each slot may face a different direction, or the like. The slots may be modified to let air out at different levels of suction.

The placement of the capsulotomy at a precise location on the surface of the lens is critical as off-centered capsulotomies may provide less IOL stability and poorer IOL optical performance. The operator may use a number of different surgical landmarks to center the capsulotomy. These include the positions of certain Purkinje images or light reflections that may be used to indicate the position of the patient's visual axis. An automated capsulotomy device, such as device 100 should allow easy centration of the cutting element 110 aligned with such Purkinje images. In the device 100 shown, the alignment of the center of the suction cup 105 with a desired surgical landmark such as a Purkinje light reflection is assisted by the placement of aiming guides, such aiming guide 190, near the center of the suction cup 105. Aiming guides may have various geometric shapes and assist in the operator's visual recognition of the location of the center of the suction cup 105 and/or the cutting element 110. Aiming guides may be manufactured onto the suction cup 105 using silicone micro-molding techniques that are well known in the art.

Once the desired alignment of the suction cup 105 has been identified, the initiation of suction must not cause a substantial shift in the position of the cutting element 110, which may result in an off-centered capsulotomy. Undesirable movement of the cutting element 110 can occur if the cutting element 110 is merely inserted into holes in the suction cup 105 that do not completely constrain cutting element 110 movements as the suction cup 105 reduces its internal volume under suction. To prevent undesirable movement, the cutting element 110 may be physically bonded to the suction cup 105, as shown in FIG. 1E.

The cutting element 110 consists of a conductive metal and the suction cup 105 may consist of silicone and thus are made as two separate parts. Hollow pockets, such as pocket 197 are disposed in the suction cup 105 to accept one or more tabs protruding from the cutting element 110. During manufacture, the tabs are placed within the corresponding hollow pockets and silicone is deposited into the hollow pockets to secure the attachment tabs in place. In some embodiments, the silicone is potted from the topside of the suction cup 105. In alternative embodiments, the silicone is potted from the bottom side of the suction cup 105. For example, during bottom potting, liquid silicone may be dispensed in each pocket. The cutting element 110 is then brought to the suction cup 105, the electrical leads 120A, 120B are fed through the lumen of the stem 125, and the attachment tabs are submerged in the liquid silicone in the potting pockets. The assembly may then be heated to cure the silicone. In some embodiments, the pockets include a thin membrane that prevents the liquid silicone from getting onto the cutting element 110. The thin membrane may be pierced by the attachment tabs as the attachment tabs are placed into the hollow pockets.

Figure 2:
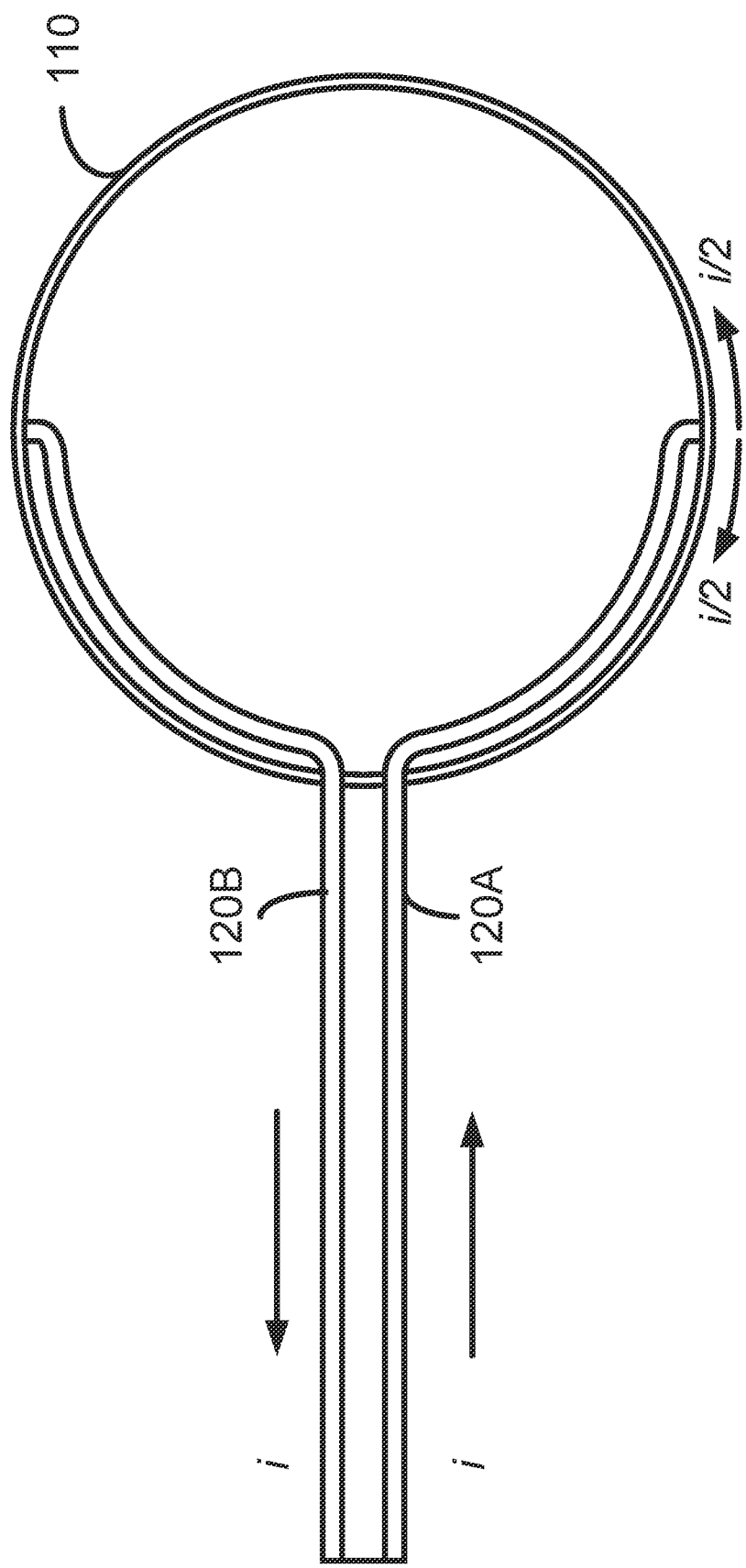
FIG. 2 illustrates the flow of current through the cutting element of the microsurgical device shown in FIG. 1A, according to one embodiment.

FIG. 2 illustrates the path of electrical current flow (i) within the cutting element 110. Upon entering the cutting element 110 through an electrical lead 120A, a portion of the current, such as one half of the current ($i_{1/2}$), travels along one half of the cutting element 110, while another portion of the current, such as the other half of the current ($i_{1/2}$), travels along the other half of the cutting element 110. Current then exits the cutting element 110 at the other electrical lead 120B. Due to the electrical resistance of the cutting element 110, the current flow causes a rapid increase in the temperature of the cutting element 110. Because of the rapid increase in temperature, the water molecules near or adjacent to the cutting element 110 and the tissue being excised vaporize rapidly and mechanically fracture the tissue along the path dictated by the portion of tissue being excised.

FIG. 3A-3F illustrate steps for using the device 100 shown in FIG. 1A, according to one embodiment. FIG. 3A a cross-section of the device 100 in close proximity to the capsular membrane 305 that encloses the lens capsule 310. In the cross-section shown, the suction cup 105 has a flow channel where the silicone is arched and thick enough to prevent collapse when the suction is applied, e.g., along tapered circumferential suction chamber 150 of the suction cup 105. The standoffs, such as standoff 185, keep the flow path under the center of the membrane open during suction. The body of the cutting element 110 illustrated has a rectangular cross-section. In alternative embodiments, the cutting element 110 may be any suitable shape, such as conical, elliptical, and the like.

The sealing contact 170 of the skirt 180 of the suction cup 105 comes into close proximity to the capsular membrane 305 which encloses the lens 310. An operator of the device centers the device 100 on the patient's visual axis. Once centered, the rigid extender has been retracted from its extended position such that the end of the rigid extender is in the neck 155 of the device 100. The rigidity of the rigid extender enables the operator to position the suction cup 105 on the visual axis over a large range of anterior chamber depth, ACD, (e.g., ACD 1.9 mm to 4.0 mm).

Figure 3B:
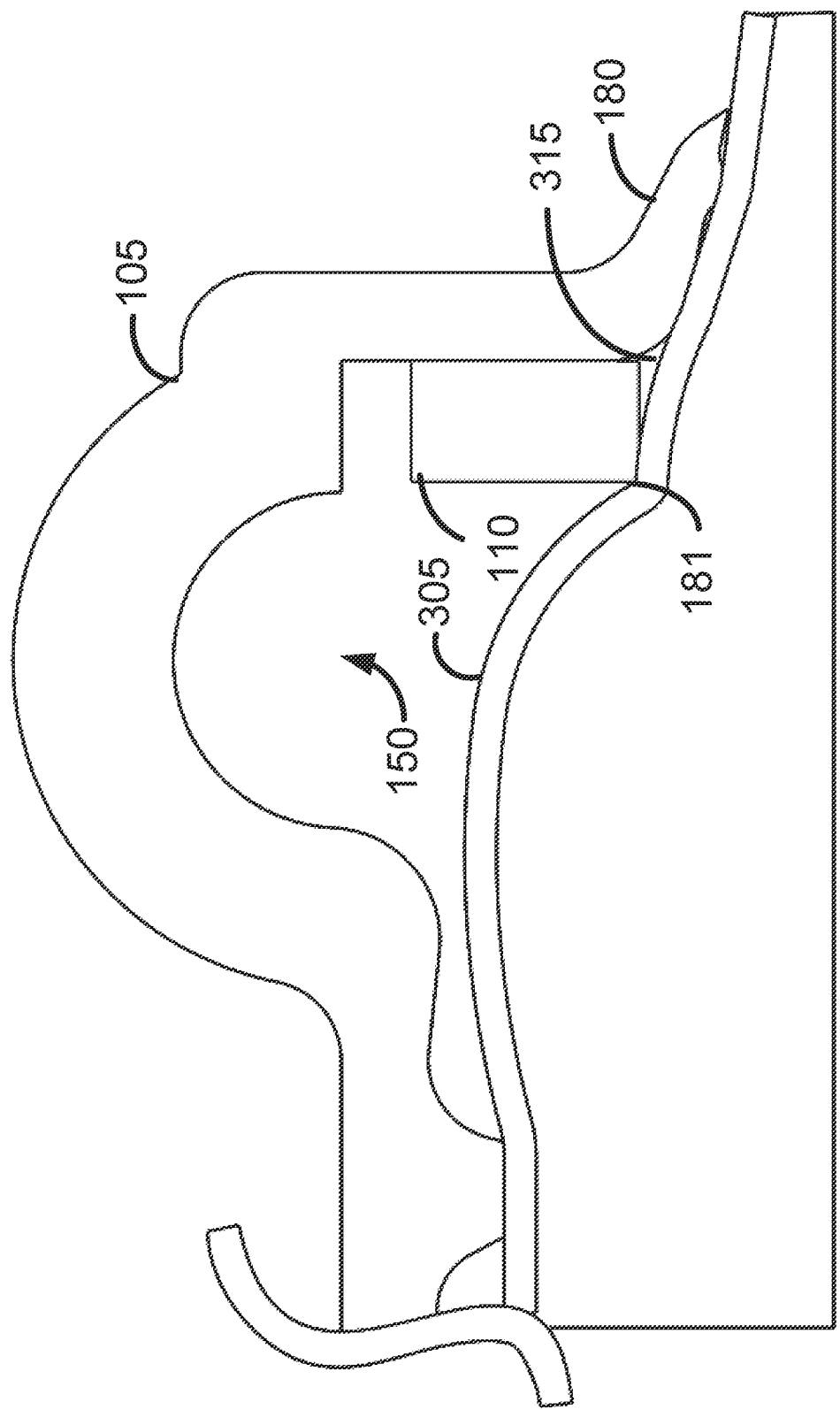

FIG. 3B illustrates the deformation of the lens 310 and suction cup 105 that occur when suction is applied to the suction cup 105. The suction forces pull the capsular membrane 305 inside the suction cup 105 and establish a contact force against the inner bottom edge 181 of the cutting element 110. Concurrently, a surface of the suction cup 105 is pulled against the outer surface of the cutting element 110. The skirt 180 of the suction cup 105 prevents contact between the capsular membrane and the outer bottom edge 183 of the cutting element 110 to limit cutting to the inner bottom edge 181 of the cutting element 110. In alternative embodiments, cutting may occur at the outer bottom edge 183 of the cutting element 110, at both the inner bottom edge 181 and outer bottom edge 183 of the cutting element 110, or the like.

A small volume 315 is created such that liquid there is trapped between the capsular membrane 305, cutting element 110, and suction cup 105. The stretching force from suction causes capsular membrane 305 to develop significant tensile stress. There is a tensile stress concentration where the capsular membrane 305 is in contact with the inner bottom edge 181 of the cutting element 110. Since this tensile stress is built up prior to the electrical discharge that makes the cut, it is already there waiting to act at the instant that the discharge occurs, and a brief flash of heat is added. In some embodiments, small volume 315 separating the outer diameter of the cutting element 110 and the capsular membrane 305 is sufficiently small that it allows the cutting element 110 to remotely cause a temperature change in the capsular membrane 305 from a distance to aid in the capsular roll up after the cutting procedure is complete.

Figure 3C:
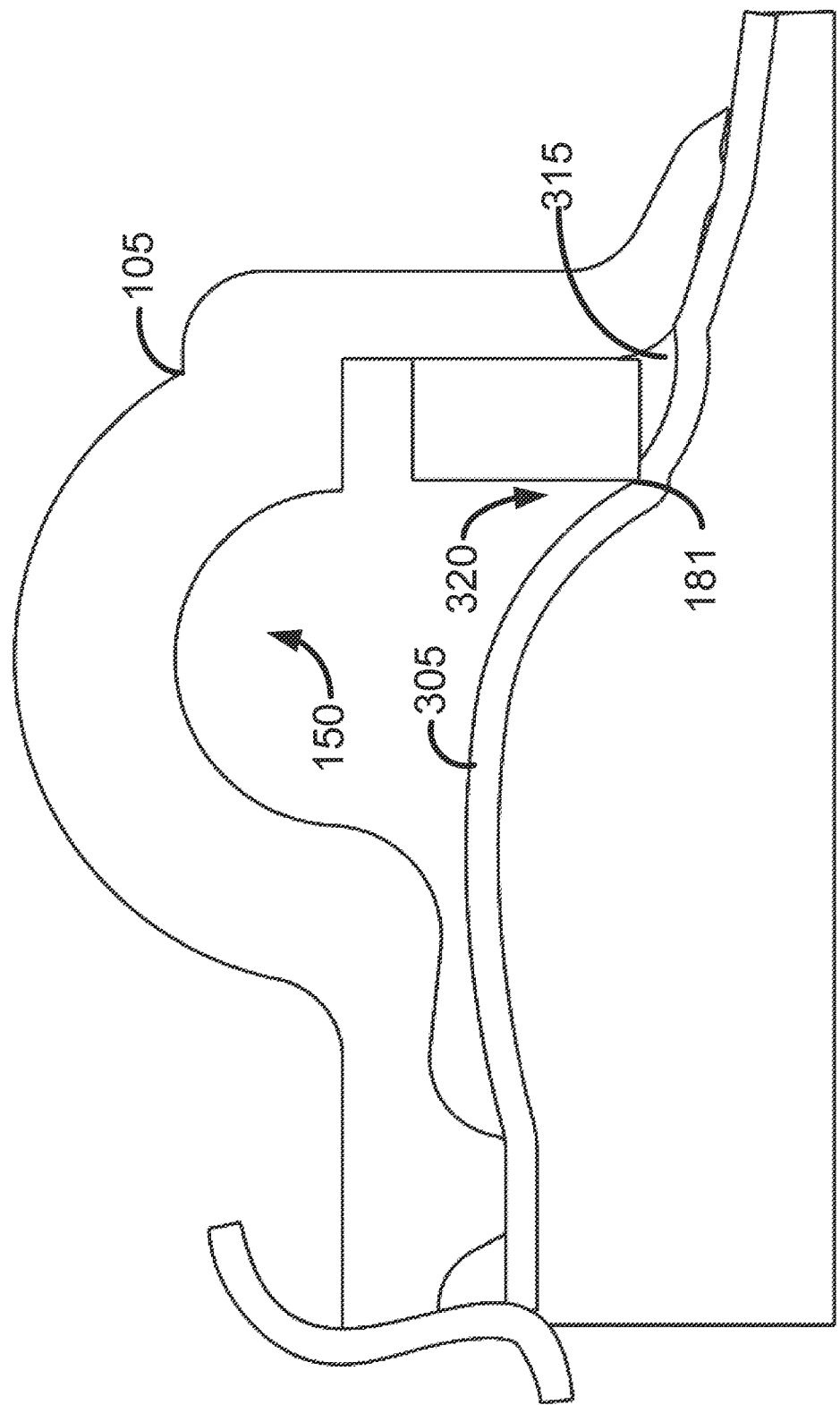

FIG. 3C illustrates the condition when the electrical discharge is occurring through the cutting element 110. Within the first few microseconds of the cutting event, the cutting element 110 heats up to a temperature hotter than the critical temperature of water. As a result, the water molecules located within a few microns of the cutting element 110 vaporize. The steam within the trapped small volume 315 cannot escape during this short time, so the pressure in the trapped small volume 315 rises. The increase in pressure results in the change of curvature that appears in the capsular membrane 305. This may also cause a change in volume of the small volume 315.

At the same time, heat is flowing from the cutting element 110 into the capsular membrane 305 at the point of contact with the cutting element 110 (e.g., the inner bottom edge 181 of the cutting element 110). As heat flows into the collagen at the point of contact between the capsular membrane 305 and the cutting element 110, the capsular membrane 305 weakens. Due to the symmetry of the device 100, equal forces and temperatures are exerted across the circumference of the cutting element 110 in contact with the capsular membrane 305. When the strength of the capsular membrane 305 is less than the forces acting to tear it, the capsular membrane 305 breaks. The forces acting to tear the capsular membrane 305 may arise from 1) the tensile stress from the suction being applied, and/or 2) the increasing pressure in the small volume 315 as a result of the steam heating up.

Because the cutting event, occurs on the millisecond time scale (e.g., 1 millisecond to 10 milliseconds), it is the inertia of the surrounding mass of material that confines the steam. It would take a great force to accelerate the surrounding mass of material during this brief time interval. During the millisecond time interval, the steam pressure builds, the material will start to move, but the capsulotomy is done by then. For example, the electrical discharge may consist of 12 pulses, 66 microseconds on, 305 microseconds off, for a total time of 4 milliseconds. This may not be enough time for the mass of material to accelerate and move. Note that the cutting of different thickness capsules or other tissues may be performed by altering the number of pulses, duration of each pulse, interpulse interval, and energy per pulse. In addition, the width of the bottom aspect of the cutting ring may be adjusted to change the spatial extent of remote temperature effects such as the roll up.

Figure 3D:
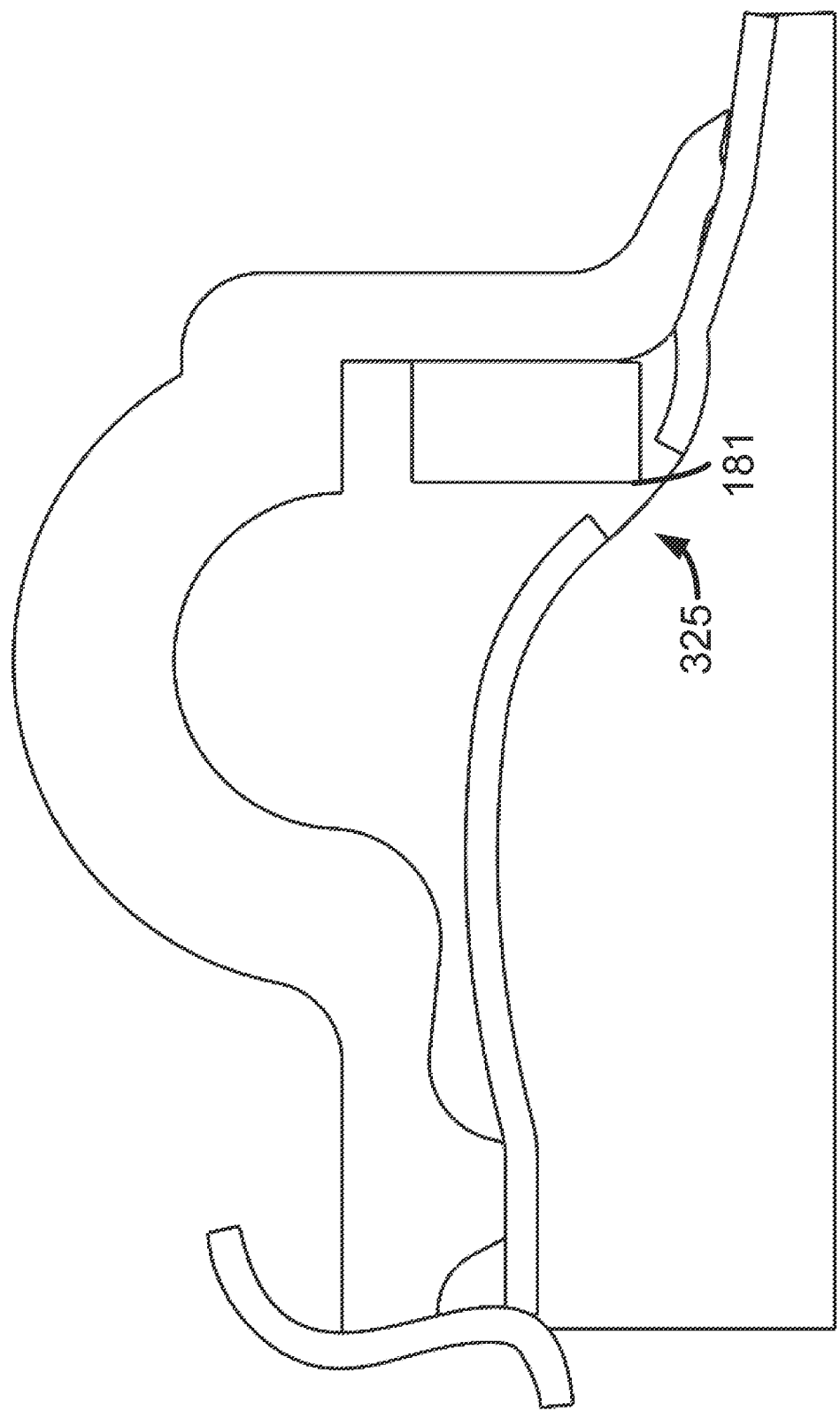

FIG. 3D illustrates the pullback 325 of the stretched capsular membrane 305 from the inner bottom edge 181 of the cutting element 110, which occurs after the electrical discharge has completed. In some embodiments, there is little inertial mass involved in this movement.

Figure 3E:
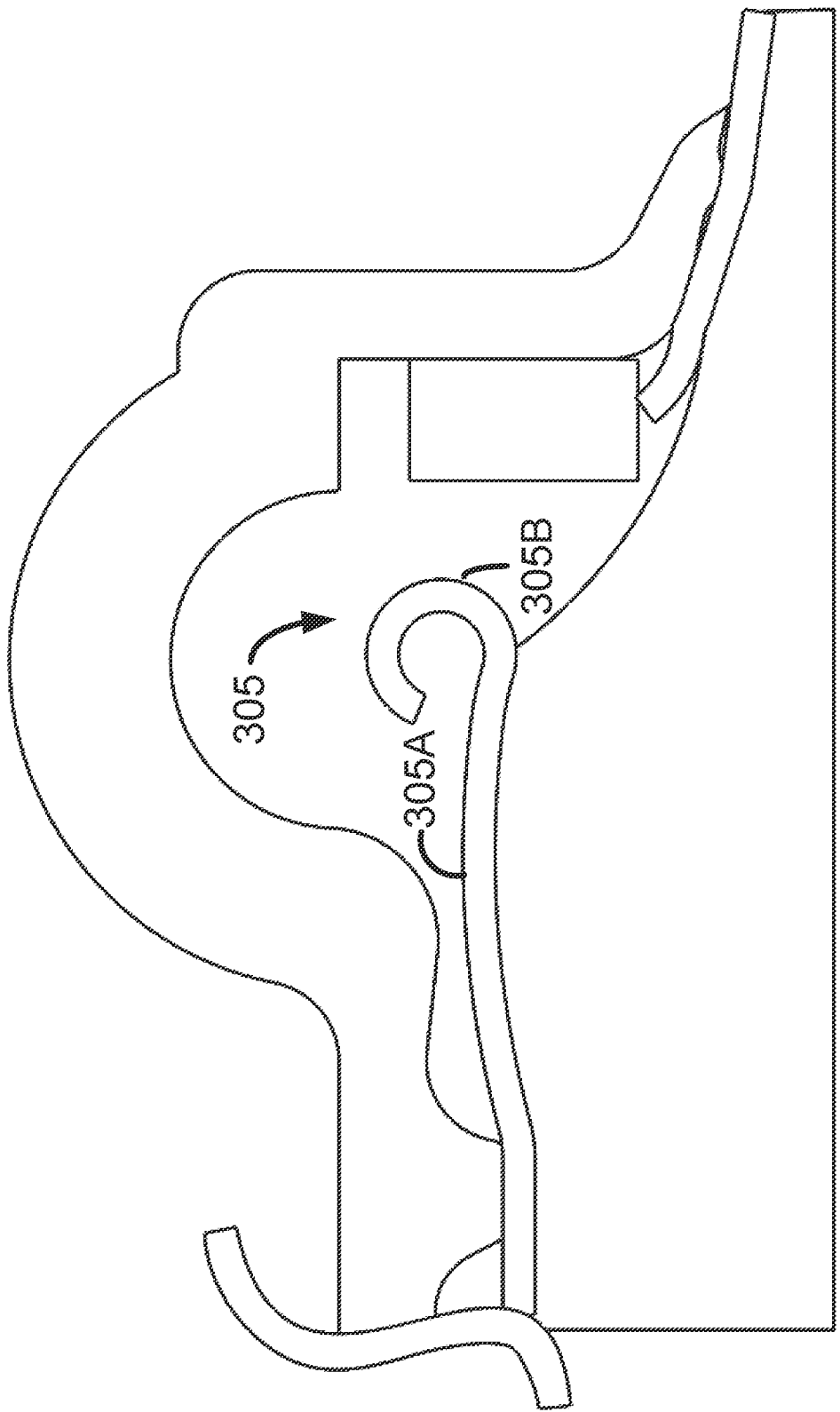

FIG. 3E illustrates the edges of the capsular membrane 305 roll up as edges cool. The edges of the capsular membrane 305 roll up because the heating method employed by the device 100 creates a temperature gradient through the thickness of the capsular membrane 305. As discussed with respect to FIG. 3B, the outer surface of the capsular membrane 305 will receive heat from the cutting element 110 through the steam that contacts it, such as the steam confined within the small volume 315. The heat causes the collagen to shrink. The collagen shrinks more at the outer surface 305A of the capsular membrane 305 than at the inner surface 305B of the capsular membrane 305 because the cutting event is too brief for significant heat to get through the steam layer and shrink the inner surface 305B of the capsular membrane 305 as much the outer surface 305A. This creates a tensile stress gradient through the thickness of the capsular membrane 305 as it cools down. The shrinkage of the collagen in the top layer pulls the edge in so it rolls up. The edge of the capsular bag can only roll up until it contacts the bottom of the cutting element 110 and/or the suction cup 105.

Figure 3F:
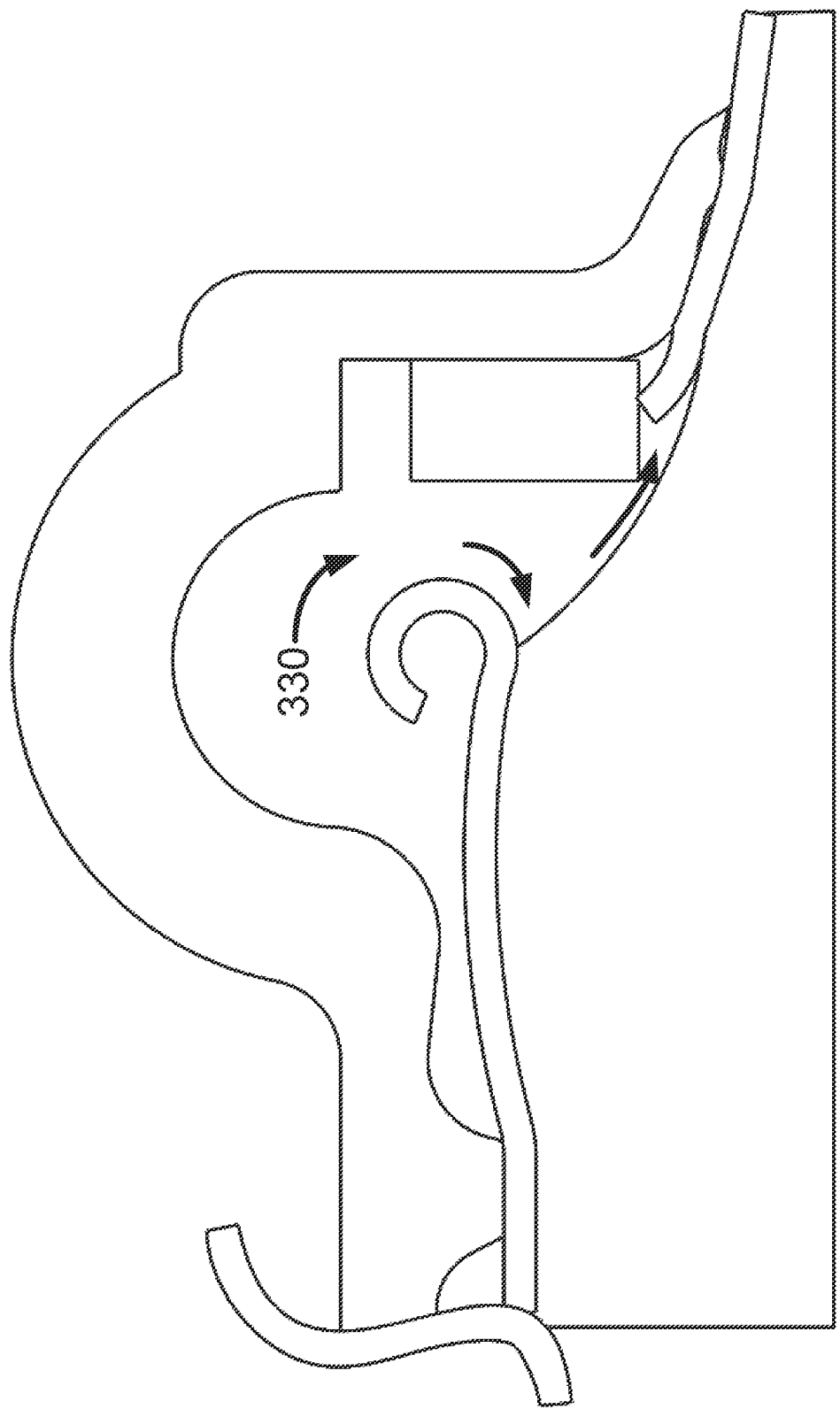

FIG. 3F illustrates the flow direction 330 of the fluid release that is performed to disengage suction and lift the suction cup 105 off the lens 310. Because the edge of the capsular bag is rolled up against the bottom of the cutting element 110 and suction cup 105, the flow at that location goes between the capsular membrane 305 and the lens 310. This performs a hydrodissection to separate capsular membrane 305 from the lens 310.

As the fluid release progresses, the edge of the capsular bag is still rolled up against the bottom of the suction cup 105, so fluid is still being directed between the capsular membrane 305 and the lens 310 to complete the hydrodissection. In some embodiments, the fluid release is performed rapidly (e.g., 0.5 seconds or less). If the release flow is fast enough, inertia of the surrounding fluid above the suction cup 105 may delay it rising long enough for the release flow to follow the path of the hydrodissection rather than simply floating off the suction cup 105. Once the edge of the capsule bag is no longer held down by the suction cup 105, the capsular bag is free to roll up under the influence of the surface stress induced by the flash of heat that came to it during the cutting event.

Phacomachine Interface for Surgical Device

Figure 4:
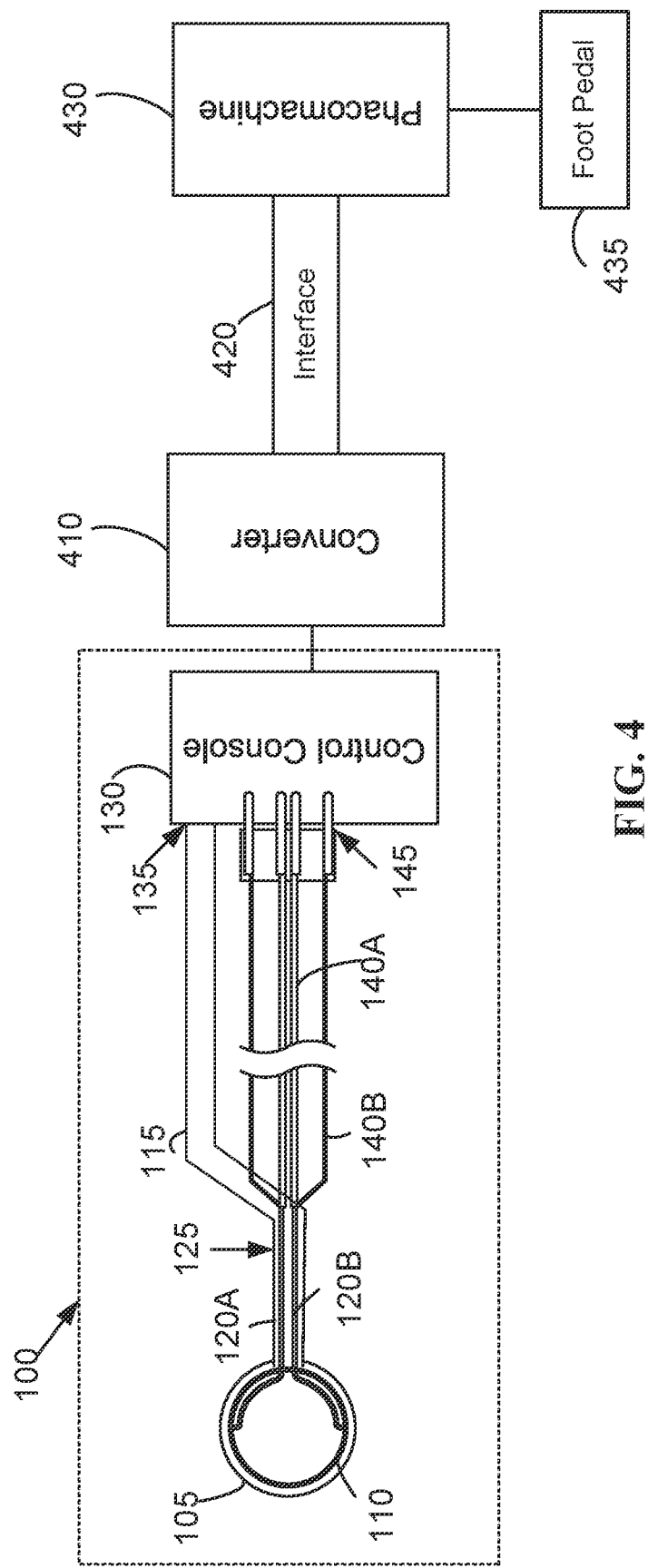
FIG. 4 illustrates an example system for performing a capsulotomy, according to one embodiment.

FIG. 4 illustrates an example system 400 for performing a capsulotomy. As shown in FIG. 4, the system 400 operates in cooperation with a phacomachine 430. The system 400 includes a microsurgical device 100, a converter 410, and an interface 420. In some embodiments, the system 400 may include different and/or additional components. Functionality described in conjunction with one or more of the components shown in FIG. 4 may be distributed among the components in different manner than described in conjunction with FIG. 4 in some embodiments. For example, the converter 410 may be a separate device from the microsurgical device 100; alternatively, some or all of the functionality of the converter 410 may be integrated with the microsurgical device 100. In another example, both the converter 410 and the interface 420 may be integrated with the microsurgical device 100.

The microsurgical device 100 is configured for cutting tissue to perform a capsulotomy. The microsurgical device 100 may include all or part of the components in the device 100 shown in FIGS. 1-3. In some embodiments, the microsurgical device 100 includes at least a cutting element 110, a stem 125, and a control console 130. The cutting element 110 may be an elastic ring coupled to the stem 125. The cutting element 110 includes a conductive surface on the bottom of the cutting element 110, which is configured to cut tissue through application of electrical current as downward pressure is applied on the elastic ring via the suction cup. The control console 130 is configured to drive a series of electrical pulses through the conductive surface of the elastic ring.

The converter 410 is electrically coupled to the microsurgical device 100. In some examples, the converter 410 may be coupled to the control console 130 of the microsurgical device 100. The converter 410 is also coupled to the interface 420 which is further connected to the phacomachine 430. In this way, the converter 410 detects a pulse of air from the phacomachine 430 via the interface 420 and produces an electrical signal based on the detected pulse of air. The produced electrical signal is then sent to the control console 130 to drive the electrical pulses for the cutting element 110 to perform a tissue cutting operation. The converter 410 may detect the number of air pulses, duration of each pulse of air, time interval between the air pulses, and/or magnitude of each pulse of air, and produce electrical signals correspondingly.

In some embodiments, the converter 410 may include an air sensor for detecting the pulse of air from the phacomachine 430. The air sensor may detect the air pressure, or a change of air pressure applied by the pulse of air. In some embodiments, the converter 410 may include a transducer for converting the detected air pressure (or change of air pressure) to electrical signals as an output. One or more air pulses can be sensed by the air sensor and used by the transducer to produce electrical signals to trigger the delivery of the capsulotomy electrical pulses to perform the lens capsulotomy. All of the parts of the converter 410 may reside outside of the control console 130. Alternatively, some of the components (e.g., transducer) may be integral components of and located inside the control console 130. In some examples, the converter 410 and interface 420 are integrated with the microsurgical device 100, the air sensor and/or the transducer may be located anywhere from the interface 420 to the control console 130.

The interface 420 connects between the phacomachine 430 and the converter 410. The interface 420 may include a connector that connects to the air port of the phacomachine 430. The interface 420 is configured to couple to an air port (e.g., vitrectomy air pulse port) of the phacomachine 430 to deliver the air pulses received from the phacomachine 430 to the converter 410. In some embodiments, the interface 420 may include air lines, fluid lines, and/or connectors that connect to other ports of the phacomachine 430, such as suction, irrigation, etc. In some embodiments, the interface 420 may be integrated with the converter 410, and/or further integrated with the control console 130 of the microsurgical device 100. The interface 420 may allow for the capsulotomy system 400 to be attached to the side of phacomachine 430, without any change in floor footprint.

In some embodiments, the interface 420 may further include electronic components, user interface, etc. so that the interface 420 functionally integrate the capsulotomy system 400 and the phacomachine 430. The capsulotomy system 400 may be controlled by the phacomachine 430, and the operations on the phacomachine 430 may be delivered to the capsulotomy system 400. For example, one or more functions of the phacomachine 430 are often performed and controlled by an operator operating a multifunctional phacomachine foot pedal 435. Operations of the capsulotomy system 400 via the phacomachine 430 may also be achieved through the use of the foot pedal 435. For instance, depressing the foot pedal 435 to a pre-determined level initiates a suction function of the microsurgical device 100. Depressing a side switch on the foot pedal 435 or depressing the foot pedal 435 to a second pre-determined level may trigger the air pulse to deliver the electrical signals for performing capsulotomy cutting. When the foot pedal 435 is released, a suction vent function may be performed, e.g., to release the suction cup 105 from a capsule of an eye, which may be facilitated by fluid delivery into the suction cup. The foot pedal may be used to control the delivery of air pulses from the phacomachine's vitrector port, including the number of air pulses, duration of each pulse of air, time interval between the air pulses, and/or magnitude of each pulse of air.

In some embodiments, with the interface 420, an operator may control all aspects of a capsulotomy procedure using the foot pedal 435, including suction, irrigation, aspiration, tissue cutting, etc. The operator initiates suction by depressing the foot pedal 435 to the appropriate position. The operator can quickly discontinue suction and/or abort the procedure by lifting the foot from the foot pedal 435. The operator can perform a tissue cutting operation (i.e., deliver energy) by depressing a pre-programmed treadle or side switch on the foot pedal. In some examples, the operator can deliver irrigation through a tip of the microsurgical device 100 to open an incision and assist in insertion of the microsurgical device 100 by depressing the foot pedal 435. The operator may release the suction cup 105 from the capsule, if needed, by activating phacomachine fluid reflux with the side switch on the foot pedal 435.

In some embodiments, the capsulotomy system 400 may further includes a cassette that can be inserted into the control console 130 to increase efficiency and security of the suction tubing and electrical connections. Additional operations may also involve the use of the cassette inserted into the control console 130 to facilitate various aspects of suction, venting of suction, surgical intraocular irrigation, irrigation for tenting the corneal incision to facilitate capsulotomy tip entry, push-rod retraction, energy pulse delivery during capsulotomy while ensuring fluidic isolation, etc.

Figure 5:
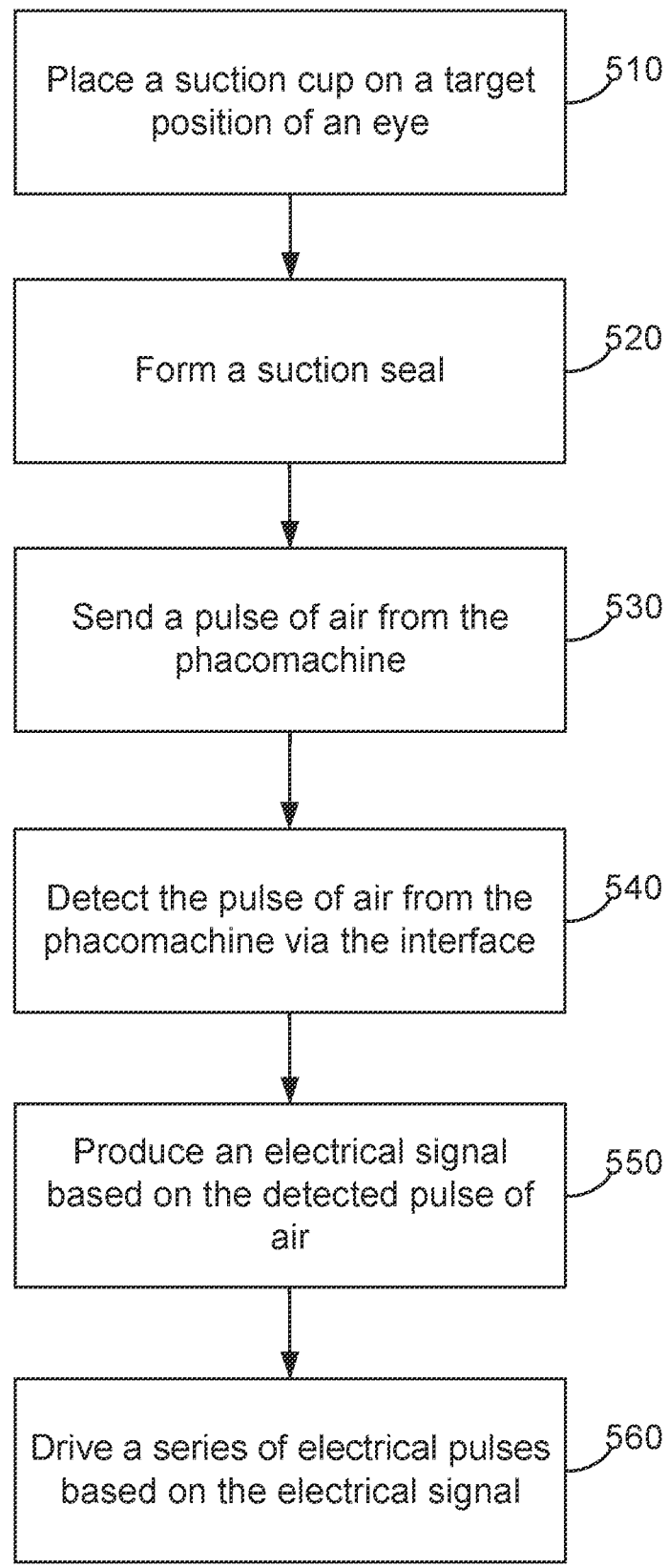
FIG. 5 is a flowchart illustrating a method for using the capsulotomy system integrated with a phacomachine to perform a capsulotomy, according to one embodiment.

FIG. 5 is a flowchart illustrating a method 500 for using a capsulotomy system to perform a capsulotomy. The capsulotomy system may be the system 400 shown in FIG. 4; alternatively, the capsulotomy system may be an integrated system including the microsurgical device 100, the converter 410 and the interface 420 shown in FIG. 4. The steps shown in FIG. 5 may be performed in cooperation of a phacomachine. Other entities may perform some or all of the steps in FIG. 5 in other embodiments. Embodiments may include different and/or additional steps, or perform the steps in different orders.

An operator places 510 a suction cup on a target position of an eye of a patient. The microsurgical device includes a suction cup that is configured to provide a water-tight seal between the edges of the suction and the tissue being excised. The target position of the eye may be the tissue to be excised, for example, lens capsule, corneal tissue, connective tissue, etc.

The operator operates to form 520 a suction seal by evacuating the material under the suction cup thereby causing a partially collapsed suction cup. The microsurgical device includes one or more suction tubes connected to the suction cup and configured to provide suction to the suction cup by evacuating the material under the suction cup thereby causing a partially collapsed suction cup and a suction seal. In some embodiments, the suction tubes may be connected to a control console of the capsulotomy system with a suction connector, and the control console provides the suction power to the suction cup via the suction tubes. Alternatively, the suction tubes and the tube connecter may connect to the phacomachine which provides the suction power to the suction cup. The operator may operate the control console and/or the phacomachine to form the suction seal. Additionally, the capsulotomy system includes an interface display that allows the user to monitor and control the suction process.

The operator proceeds to send 530 a pulse of air from the phacomachine to initiate a tissue cutting operation. Operations of the phacomachine may be achieved through the use of a foot pedal. By depressing a side switch on the foot pedal or depressing the foot pedal to a second pre-determined level, the operator can generate the pulse of air. Air pulses can also be delivered by the phacomachine through touch screen operation or other methods such as a remote control.

The converter of the capsulotomy system detects 540 the pulse of air from the phacomachine via the interface of the capsulotomy system. The interface is coupled to an air port of the phacomachine, and the pulse of air is sent via an air line to a converter of the capsulotomy system. The converter may detect the number of air pulses, duration of each pulse of air, time interval between the air pulses, and/or magnitude of each pulse of air.

The converter produces 550 an electrical signal based on the detected pulse of air. The converter may produce electrical signals corresponding to the detected number of air pulses, duration of each pulse of air, time interval between the air pulses, and/or magnitude of each pulse of air. In some embodiments, the converter may include an air sensor for detecting and convert the detected air pressure to electrical signals as an output to the control console.

In response to the received electrical signal, the control console of the capsulotomy system drives 560 a series of electrical pulses based on the electrical signal. In some embodiments, the capsulotomy system may generate the series of electrical pulses corresponding to the electrical signal so that the series of electrical pulses are associated with the number of air pulses, duration of each pulse of air, time interval between the air pulses, and/or magnitude of each pulse of air. The control console drives the electrical energies through a conductive surface of the cutting element (e.g., an elastic ring) of the capsulotomy system to perform a tissue cutting operation (e.g., capsulotomy).

With the interface and the converter of the capsulotomy system, full control of all aspects of the capsulotomy procedure may be achieved by the operator using the phacomachine's foot pedal. The capsulotomy system and the phacomachine can be programmed at the operator's discretion to automate certain aspects of the capsulotomy procedure, thus, improving ergonomic efficiency in the operating room and ease of operation to enhance clinical outcome and patient safety.

Figure 6:
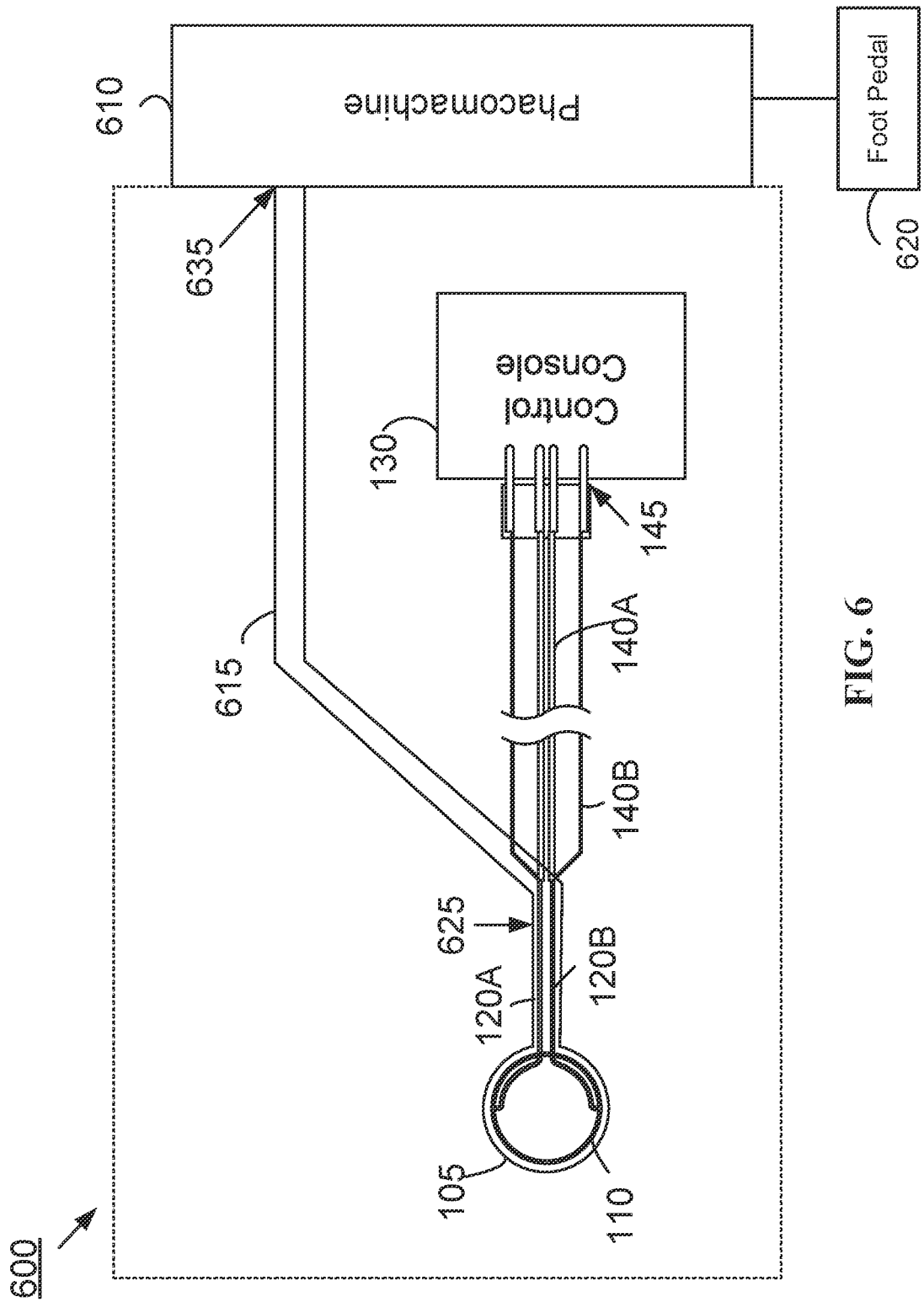
FIG. 6 illustrates another example system for performing a capsulotomy, according to one embodiment.

FIG. 6 illustrates another example system 600 for performing a capsulotomy. As shown in FIG. 6, the system 600 operates in cooperation with a phacomachine 610. The system 600 is similar to the microsurgical device 100 as described in former sections and as shown in FIGS. 1-3. The system 600 may be a modified microsurgical device 100 that is configured to provide irrigation and/or aspiration functions in a capsulotomy. Similar to the microsurgical device 100, the system 600 may include all or part of the components in the device 100 shown in FIGS. 1-3. As shown in FIG. 6, the system 600 includes at least a cutting element 110, a suction cup 105, a stem 625, a control console 130, a tube interface 615 and one or more tube connectors 635. Functionality described in conjunction with one or more of the components shown in FIG. 6 may be distributed among the components in different manner than described in conjunction with FIG. 6 in some embodiments. In some embodiments, the system 600 may include different and/or additional components. For example, the system 600 may further include the converter 410 and the interface 420 as shown in FIG. 4 to integrate the control of the system 600 and the phacomachine 610.

The cutting element 110 may be an elastic ring coupled to the stem 625. The cutting element 110 includes a conductive surface on the bottom of the cutting element 110, which is configured to cut tissue through application of electrical current as downward pressure is applied onto the elastic ring as the contents of the suction cup is evacuated by suction. The suction cup 105 is configured to provide a water-tight seal between the edges of the suction and the tissue being excised. The suction cup 105 and cutting element 110 are located at a distal end of the stem 625.

The tube interface 615 is configured to couple to a fluid line of the phacomachine 610 to receive an irrigation fluid from the phacomachine 610. One end of the tube interface 615 may connect with one or more ports of the phacomachine 610 by the one or more tube connectors 635; and the other end of the tube interface 615 may be coupled to the stem 625.

The capsulotomy system 600 is configured to deliver the received irrigation fluid into a space between the suction cup 105 and a surface of an eye so as to provide the irrigation function. For example, fluid channels in the stem 625 may deliver the fluid into a space, e.g., an anterior chamber of the eye to maintain the pressure within the anterior chamber. In another example, the fluid channels in the stem 625 may deliver the fluid into a space between a top surface of the suction cup 105 and an inside surface of an eye. The capsulotomy system 600 may be configured to remove a portion of the material or fluid under the suction cup 105 with aspiration power to perform a suction operation. In this way, the pressure between the suction cup 105 and the surface of the eye decreases, and a suction seal forms between the suction cup 105 and the surface of the eye. Then the control console 130 may drive a series of electrical pulses through the conductive surface of the elastic ring to perform a tissue cutting operation as needed. In some embodiments, after the suction seal is formed, the user may break the suction seal by delivering additional irrigation fluid into the suction cup 105 and the surface of the eye. In this way, the suction cup 105 may be movable relative to the eye, and a new suction seal may be reformed at a desired location. With the irrigation and aspiration function, the operator may use the capsulotomy system 600 to remove or dilute the viscous OVD present under the suction cup 105, lift the suction cup 105 off the capsule with reverse suction, or re-position the capsulotomy in a different location on the capsule. In some examples, the irrigation and aspiration functions may help remove the trapped air bubbles in a microsurgical device, an anterior chamber, a surgical setup before or during the capsulotomy process. In some embodiments, the control console 130 of the system 600 may be integrated with the phacomachine 610 in a similar way as shown in FIG. 4. In this way, all aspects of a capsulotomy procedure, such as, suction, irrigation, aspiration, tissue cutting, etc., may be controlled using the phacomachine 610 and its foot pedal 620.

Referring back to the tube interface 615, the tube interface 615 may be configured differently based on the functions it includes. In one example, the system 600 includes separate fluid delivery and suction tubes and fluid delivery and suction connectors (e.g., the suction tube 115 and the suction connector 135 shown in FIG. 1A). The fluid tube of the tube 615 is configured to receive the irrigation fluid from the fluid line of the phacomachine 610. The fluid tube 615 and the suction tube may connect to a proximal end of the stem 625 at a same connection point. Inside the stem 625, the suction tube and the fluid tube share the same channel that is coupled to the suction cup 105. In this way, the irrigation and aspiration functions are controlled separately and used alternatively.

In another example, the suction tube and the fluid tube in the tube interface 615 may connect to the stem 625 at different connection points. For example, the suction tube and the fluid tube may be connected to the opposite ends of the stem 625. While the suction tube connects to a proximal end of the stem 625, the fluid tube of the tube interface 615 may connect to a distal end of the stem 625. The connection point of the fluid tube is closer to the suction cup 105 compared to the suction tube connection point at the stem 625. The suction tube and the fluid tube still share the same inlet/outlet opening in the suction cup 105.

In still another example, the irrigation fluid enters the suction cup 105 through its own inlet (i.e., irrigation inlet), and the suction/aspiration fluid exits the suction cup 105 through another outlet (i.e., aspiration outlet). The irrigation inlet and aspiration outlet do not share the same opening. They may also be of any shape or size and located anywhere in the suction cup that is appropriate for the necessary irrigation flux and aspiration flux during operation of the capsulotomy.

In some embodiments, the irrigation inlet may be a slit opening within the suction cup 105. Due to its slit geometry and the durometer of the silicone used in suction cup molding, the irrigation inlet may be normally in a "closed" state. During application of suction, the irrigation opening further closes as the suction cup 105 may have a tendency to collapse under the suction pressure. When irrigation is desired, the pressure generated by the incoming irrigation fluid that is pushed forward by a remotely located force generation mechanism for example, in the phacomachine, causes the irrigation opening to open and allow inflow of irrigation fluid. The aspiration may or may not be functioned at the same time. If aspiration/suction is activated at the same time as the irrigation function, as long as the entry of irrigation fluid is greater than outflow, there will be net entry of irrigation fluid under the suction cup 105. With this configuration, both aspiration and irrigation functions may be operated at the same time. Depending on which flow is greater, net aspiration or net irrigation can be achieved. Additionally, upon disengagement of the suction cup 105 from the capsule post capsulotomy, any OVD or debris may remain in the aspiration line and may not be pushed back into the anterior chamber when the irrigation is applied. The debris remains in the aspiration line since a dedicated irrigation inlet into the suction cup 105 may be used to use irrigation fluid to help lift the suction cup 105 off the capsule.

Figure 7:
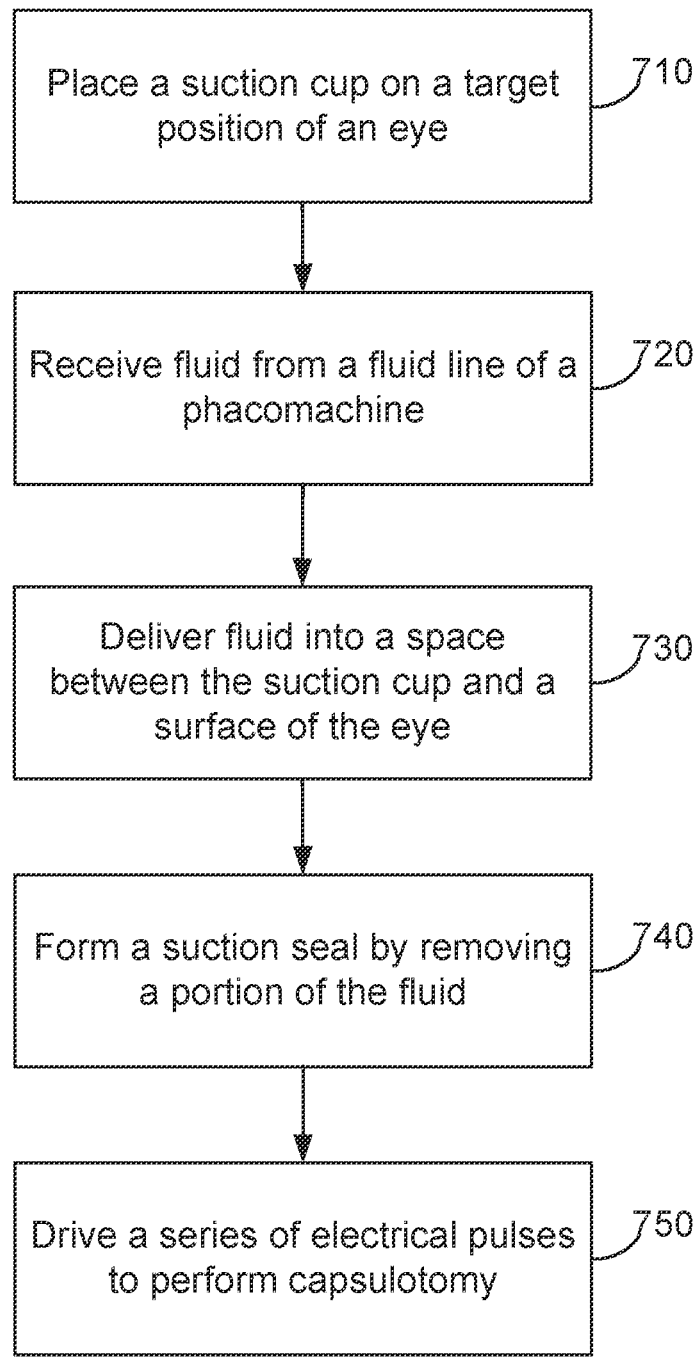
FIG. 7 is a flowchart illustrating another method for using the capsulotomy system to perform a capsulotomy, according to one embodiment.

FIG. 7 is a flowchart illustrating a method 700 for using a capsulotomy system to perform a capsulotomy. The capsulotomy system may be the system 600 shown in FIG. 6. The steps shown in FIG. 7 may be performed in cooperation with a phacomachine. Other entities may perform some or all of the steps in FIG. 7 in other embodiments. Embodiments may include different and/or additional steps, or perform the steps in different orders.

An operator places 710 a suction cup on a target position of an eye of a patient. The capsulotomy system includes a suction cup that is configured to provide a water-tight seal between the edges of the suction and the tissue being excised. The suction cup is coupled to an elastic ring which includes a conductive surface for cutting tissue. The target position of the eye may be the tissue to be excised, for example, lens capsule, corneal tissue, connective tissue, etc.

The capsulotomy system receives 720 fluid from a fluid line of a phacomachine. The capsulotomy system includes an interface that is coupled to the fluid line of the phacomachine so that the capsulotomy system receives the fluid from the phacomachine via the interface. The fluid may be used for irrigation or other purposes.

The capsulotomy system 730 delivers the received fluid into a space between the suction cup and a surface of the eye. The space may be an anterior chamber of the eye. Alternatively, the space may be between a top surface of the suction cup 105 and an inside surface of an eye. In some embodiments, the fluid is injected into the anterior chamber to maintain the pressure within the anterior chamber.

The capsulotomy system forms 740 a suction seal by removing a portion of the fluid or material from under the suction cup. The phacomachine's aspiration function can be used by the capsulotomy system to remove a portion of the fluid with a suction power to perform an aspiration operation. The aspiration operation causes the pressure between the suction cup and the surface of the eye decrease to form the suction seal.

In some embodiments, the system may use the delivered fluid as irrigation fluid to remove or dilute the viscous OVD present under the suction cup. In some other embodiments, the system may deliver fluid to reverse the suction, lift the suction cup off the capsule, and/or re-position the capsulotomy in a different location on the capsule. Additionally, the system may use the fluid to remove the trapped air bubbles in the capsulotomy system, anterior chamber, during surgical setup before or during the capsulotomy process.

After the suction seal is formed, the capsulotomy system drives 750 a series of electrical pulses through the elastic ring to perform the capsulotomy. In some embodiments, the capsulotomy system may generate the series of electrical pulses corresponding to the electrical signal so that the series of electrical pulses are associated with the number of air pulses, duration of each pulse of air, time interval between the air pulses, and/or magnitude of each pulse of air. In some embodiments, the control console of the capsulotomy system may be integrated with the controller (e.g., a foot pedal) of a phacomachine, and full control of all aspects of the capsulotomy procedure may be achieved by the operator using the phacomachine foot pedal.

Depending on the configuration of the capsulotomy system, the method 700 for using the capsulotomy system may include different and/or additional steps and/or repeat steps. For example, the user may desire to re-position the suction cup and create the capsulotomy at a different location on a surface of the eye. In this case, there is an initial suction performed using aspiration followed by fluid delivery to reverse suction and push the suction cup off the surface of the eye. This will be followed by a re-positioning of the suction cup, followed by a repeat of suction using the aspiration function.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims. As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

What is claimed is:

1. A method for performing a capsulotomy using a capsulotomy device, comprising:
   receiving fluid from a fluid line of a phacomachine via an interface of the capsulotomy device;
   delivering the received fluid into a space between a suction cup of the capsulotomy device and a surface of an eye via an irrigation inlet opening of the suction cup, wherein the suction cup forms a single chamber that forms the space with the surface of the eye;
   forming, via an aspiration outlet opening of the suction cup, a suction seal between the suction cup and the surface of the eye by removing at least a portion of received fluid from the space using suction from an aspiration line of the phacomachine, wherein the interface is configured to simultaneously enable the fluid from the phacomachine to enter the suction cup via the fluid line and the irrigation inlet opening and to enable the received fluid to be aspirated from the suction cup to the phacomachine via the aspiration outlet opening and the aspiration line;
   driving, by a control console of the capsulotomy device, a series of electrical pulses through an elastic ring of the capsulotomy device to perform the capsulotomy, wherein the elastic ring comprises a conductive surface for tissue cutting; and
   breaking, via the irrigation inlet opening, the suction seal by delivering additional fluid received from the fluid line, into the space.

2. The method of claim 1, wherein the interface includes a fluid tube coupled to a stem and connected to a channel housed in the stem.

3. The method of claim 2, wherein the interface includes a suction tube configured to remove the received fluid from the space.

4. The method of claim 3, wherein the fluid tube and the suction tube are each coupled to the stem at a same connection point.

5. The method of claim 3, wherein the fluid tube and the suction tube are coupled to opposite ends of the stem.

6. The method of claim 1, wherein the irrigation inlet opening is different from the aspiration outlet opening.

7. The method of claim 1, wherein the interface includes a connector that connects to at least one of a suction port or an irrigation port of the phacomachine.

8. The method of claim 1, further comprising coupling the control console with a foot pedal of the phacomachine so that the foot pedal controls one or more functions of the control console.

* * * * *